(12) United States Patent
McCain et al.

(10) Patent No.: US 12,367,956 B2
(45) Date of Patent: Jul. 22, 2025

(54) ELECTRONIC UNITS FOR MEDICAL DEVICES

(71) Applicants: Aisha McCain, Pittsburg, CA (US);
Annmarie Sheets, Pittsburg, CA (US)

(72) Inventors: Aisha McCain, Pittsburg, CA (US);
Annmarie Sheets, Pittsburg, CA (US)

(73) Assignee: Create To Overcome LLC, Pittsburg, CA (US)

( * ) Notice: Subject to any disclaimer, the term of this patent is extended or adjusted under 35 U.S.C. 154(b) by 142 days.

(21) Appl. No.: 18/242,255

(22) Filed: Sep. 5, 2023

(65) Prior Publication Data

US 2023/0410971 A1 Dec. 21, 2023

Related U.S. Application Data

(63) Continuation-in-part of application No. 17/736,556, filed on May 4, 2022, now Pat. No. 11,749,091.

(Continued)

(51) Int. Cl.
| | |
|---|---|
| *G16H 20/13* | (2018.01) |
| *A61B 5/11* | (2006.01) |
| *A61B 5/117* | (2016.01) |
| *A61B 90/90* | (2016.01) |
| *A61M 5/20* | (2006.01) |
| *A61M 15/00* | (2006.01) |

(Continued)

(52) U.S. Cl.
CPC ............ *G16H 20/13* (2018.01); *A61B 5/1112* (2013.01); *A61B 5/117* (2013.01); *A61B 90/90* (2016.02); *A61M 5/2033* (2013.01); *A61M 15/0001* (2014.02); *A61M 16/0003* (2014.02); *A61N 1/3904* (2017.08); *A61N 1/3925* (2013.01); *A61M 2205/18* (2013.01); *A61M 2205/3553* (2013.01); *A61M 2205/3584* (2013.01); *A61M 2205/3592* (2013.01); *A61M 2205/502* (2013.01); *A61M 2205/581* (2013.01); *A61M 2205/582* (2013.01); *A61M 2205/587* (2013.01); *A61M 2205/6054* (2013.01)

(58) Field of Classification Search
CPC .................................. G08B 21/24; G08B 7/06
See application file for complete search history.

(56) References Cited

U.S. PATENT DOCUMENTS

| | | | |
|---|---|---|---|
| 10,204,213 B2* | 2/2019 | Doswell | ............... A61B 5/1112 |
| 2011/0226242 A1* | 9/2011 | Von Hollen | ...... A61M 15/0023 |
| | | | 128/203.12 |

(Continued)

*Primary Examiner* — Kam Wan Ma
(74) *Attorney, Agent, or Firm* — Cynthia S. Lamon; Lamon Patent Services

(57) ABSTRACT

A system is provided to assist a user having a medical emergency including computerized electronic units attached to or adhered to emergency medication dispensers or emergency medical devices. And the application is also provided on users' smartphones enabling registration of the electronic units and type of emergency medication or medical device they are adhered to or attached to. The application provides a user interface enabling a first user to activate alerts on the electronic unit to locate the medical dispenser or emergency medical device. The user interface enables the users to activate emergency medical help causing a connected server to locate a second user to assist in a vicinity of the user requiring medical assistance having the medication or medical device required by the first user.

12 Claims, 15 Drawing Sheets

Related U.S. Application Data

(60) Provisional application No. 63/221,213, filed on Jul. 13, 2021, provisional application No. 63/220,186, filed on Jul. 9, 2021.

(51) Int. Cl.
*A61M 16/00* (2006.01)
*A61N 1/39* (2006.01)

(56) References Cited

U.S. PATENT DOCUMENTS

| | | | |
|---|---|---|---|
| 2014/0000598 A1* | 1/2014 | Sutherland | G16H 20/10 |
| | | | 128/203.12 |
| 2016/0144141 A1* | 5/2016 | Biswas | A61M 15/009 |
| | | | 128/200.23 |
| 2016/0325057 A1* | 11/2016 | Morrison | A61B 5/087 |
| 2017/0325734 A1* | 11/2017 | Sutherland | A61M 15/0041 |
| 2019/0021400 A1* | 1/2019 | Fornarelli | A24F 40/60 |

* cited by examiner

ELECTRONIC UNITS FOR MEDICAL DEVICES

CROSS-REFERENCE TO RELATED DOCUMENTS

The present invention is a Continuation-in-Part to U.S. application Ser. No. 17/736,556, filed May 4, 2022 which claims priority to a U.S. provisional patent application Ser. No. 63/221,213 entitled ELECTRONIC AUTO-INJECTOR SLEEVE DEVICE filed on Jul. 13, 2021, and to a U.S. provisional patent application Ser. No. 63/220,186 entitled ELECTRONIC INHALER SLEEVE DEVICE, filed on Jul. 9, 2021, disclosure of which is included herein at least by reference.

BACKGROUND OF THE INVENTION

1. Field of the Invention

The present invention is in the field of medical devices and pertains particularly to methods and apparatus for medically purposed aftermarket devices and pertains particularly to a material covering enhanced by electronic for encasing or otherwise encapsulating an emergency medication dispensing device.

2. Discussion of the State of the Art

Medications for breathing problems, such as asthma and chronic obstructive pulmonary disease (COPD), are commonly delivered directly to the lungs. These medications include albuterol and steroids, among others. A meter dose inhaler (MDI) is commonly termed an inhaler in the art. Most of the inhaler devices are MDIs. For example, the drug albuterol delivered by MDI is the fastest way to reverse an asthma attack. The medicine allows the muscles around branches of the lungs to relax. Asthma is a common, chronic respiratory disease that affects approximately 26 million people in the US. It is the most common chronic disease in childhood, affecting an estimated 7 million children. The estimate of lost work and school time from asthma is approximately 100 million days of restricted activity. Approximately 500,000 annual hospitalizations (40.6% in individuals aged 18 years or younger) are due to asthma. Each year, an estimated 1.7 million people (47.8% of them aged 18 years or younger) require treatment in an emergency department. For 2010, the annual expenditures for health and lost productivity due to asthma was projected to be $20.7 billion.

Patients with poorly controlled asthma develop long-term changes over time (i.e., with airway remodeling). This can lead to chronic symptoms and a significant irreversible component to their disease. Mortality in the US is approximately 1 per 100,000, and death often occurs in young people due to treatment and management failure. People who live with asthma must keep their inhaler with them in body of an attack, however, it is easy for a person to forget or lose the inhaler. Asthma can quickly become so severe that speaking or calling for help is impossible. Seconds can make the difference between life and death. While many medical devices including MDIs have been fabricated with electronic capabilities including enabling a mobile application to track device usage, the capabilities are brand specific and add to the costs of the device itself limiting availability to certain manufactured devices.

Medications for severe allergic reactions in people, such as those due to insect bites, insect stings, certain foods, drugs, or other substances are commonly delivered directly to the muscle (intramuscular) or to the skin (subcutaneous). The delivered medication is typically Epinephrine. Epinephrine may be delivered through a needle that is part of an auto-injector device, an example of which is an Auto-Injector™ device, a popular brand of such auto-injector devices. Epinephrine acts very swiftly once delivered and improves breathing, stimulates the heart muscle, raises a dropping blood pressure reading, reverses hives, and reduces swelling of the face, lips, and throat. Severe allergies affect approximately 50 million people in the US. Allergic reactions occur in approximately 40% of children. Allergic reactions are the sixth leading cause of chronic illness in the United States. The estimate of lost work and school time from allergic reactions is approximately 32 hours per week per sufferer during peak allergy seasons. Severe allergic reactions to foods result in approximately 30,000 emergency room visits per year in the United States.

The annual cost of treating allergic reactions exceeds 18 billion dollars. About 32 million people have food allergies with shellfish leading, followed by peanuts and then tree nuts. In children milk is in the top spot for an allergic food followed by eggs and then peanuts. Penicillin takes the top spot for those with drug allergies. People who live with sever allergies must keep their auto-injector device (Body) with them constantly in body of an attack, however, it is easy for a person to forget or lose an Body™ or any other brand of auto-injector device. An allergic reaction can quickly become so severe that speaking or calling for help is impossible. Seconds can make the difference between life and death. People may misplace or lose their epi pens and are at risk until they procure a replacement device.

Therefore, what is clearly needed is an electronically enhanced elastic material sleeve that may be custom fit to at least one form of a dedicated aftermarket emergency medication dispensing device carried by a user for medical maintenance and or medical emergency applications.

BRIEF SUMMARY OF THE INVENTION

A system is provided enabled to assist a user during a medical emergency comprising a plurality of electronic units each having a unique identifier, adapted to attach, one each, to emergency medication dispensing devices and emergency medical devices. Each electronic unit includes a housing formed by a wall or dual wall of flexible material having a diameter and a length, a microprocessor and associated circuitry encapsulated entirely within a thickness of the wall of the housing, the circuitry including at least a microprocessor, wireless communications capability, a transceiver capable of cellular and satellite communication, and GPS. At least one battery is included in this embodiment encapsulated within the thickness of the wall providing power to the microprocessor and the circuitry, alert mechanisms including at least one LED at least partially encapsulated within the wall of the housing is included and may be visible from outside of the wall, at least one sound emitter and a vibrating motor.

An Internet connected server is included in this embodiment storing and executing software from non-transitory storage medium and a plurality of GPS enabled smartphones storing and executing an instance of the software. Wherein the instance of the software stored on the smartphones may provide a first user and a second user with a user interface enabling the first and second users to subscribe to the software uploading personal identification and location data, enabling the first user to register the unique identifier of one or more first electronic units, of the plurality of electronic units, each first electronic unit associated and adhered to an emergency medication dispenser, identifying the emergency medication being dispensed or an emergency medical device, and enabling the second user to register the unique identifier of one or more second electronic units, of the plurality of electronic units, each second electronic unit associated and adhered to an emergency medication dispenser, identifying the emergency medication being dispensed or an emergency medical device, wherein communication is established between the one or more first and second electronic units, the smartphones and the server and the server is enabled to track location of the first and second electronic units and the smartphones via the GPS.

In one embodiment, the first user may require an emergency medication contained within the emergency medication dispenser or may require an emergency medical device associated with the one or more first electronic units, and could initiate the alert mechanisms on the electronic unit via the user interface in order to locate the emergency medication or emergency medical device. In this embodiment, the first user may initiate a medical emergency alert to the server via interaction with an indicia on the user interface based upon an inability to administer the required emergency medication or emergency medical device and the server broadcasts an alert to all user interfaces on smartphones associated with second users determined to be within a vicinity of the first user. The server then identifies and locates the second user within the vicinity having a closest location to the first user, the second user having the registered second electronic unit adhered to an associated second emergency medication or second emergency medical device matching the emergency medication or emergency medical device required by the first user.

In one embodiment, the second user indicates an ability to assist the first user with the emergency medicine or emergency medical device via interaction with second indicia on the user interface of the second smartphone associated with the second user and may cause presentation of a map in the user interface of the identified second user directing the identified second user to the location of the first user. In an instance where a second user is not within the vicinity, the instance of software on the smartphone alerts emergency medical professionals to the location of the first user.

In all embodiments, the emergency medication dispenser may be any dispenser from a list including a cylinder with adjustable regulator, an epi pen, a metered spray bottle, a nasal spray bottle, an oral inhaling device, a syringe and a medication dispenser having an inner volume and a removable cap, the medication dispenser integrated with an electronic unit of the electronic unit. Emergency medications may include any medication from a list including oxygen, epinephrine, nitroglycerine, diphenhydramine, albuterol/salbutamol, aspirin, glucose, atropine, hydrocortisone, morphine or nitrous oxide, naloxone, lorazepam or midazolam and flumazenil, although this list is not exhaustive. Additionally, the emergency medical devices may be any devices from a list including an automated external defibrillator (AED), a rescue suction device, an oxygen mask, electrosurgical units and a portable ventilator. In order to accommodate shapes and sizeds of the dispensers and devices, the electronic unit is in a form of a tubular sleeve or patch with adhesive.

DETAILED DESCRIPTION OF THE INVENTION

In various embodiments described in enabling detail herein, the inventor provides a unique electronic material sleeve fitted to an emergency medication dispensing device, the sleeve adapted to be tracked and communicated with via digital wireless communication. A goal of the present invention is to enable a user to locate his or her emergency medication dispensing device using a mini tracking fob device or using a mobile computing appliance that may or may not host an executable tracking application. Fob devices are small electronic devices which communicate an electronic token wirelessly to access, activate or unlock another device.

Another goal of the invention is to enable automatic and manual emergency alert reporting from the electronic material sleeve to a third-party emergency responder service that may dispatch a medical response person or personnel locally. A further goal of the invention is to enable data collection from memory provided in the sleeve electronic for subsequent utilization in locating the electronic sleeve, monitoring the charge state of the electronic sleeve, or in monitoring a patient's medical dispense frequency and pattern including current canister volume. The present invention is described using the following examples, which may describe more than one relevant embodiment falling within the scope of the invention.

Figure 1:
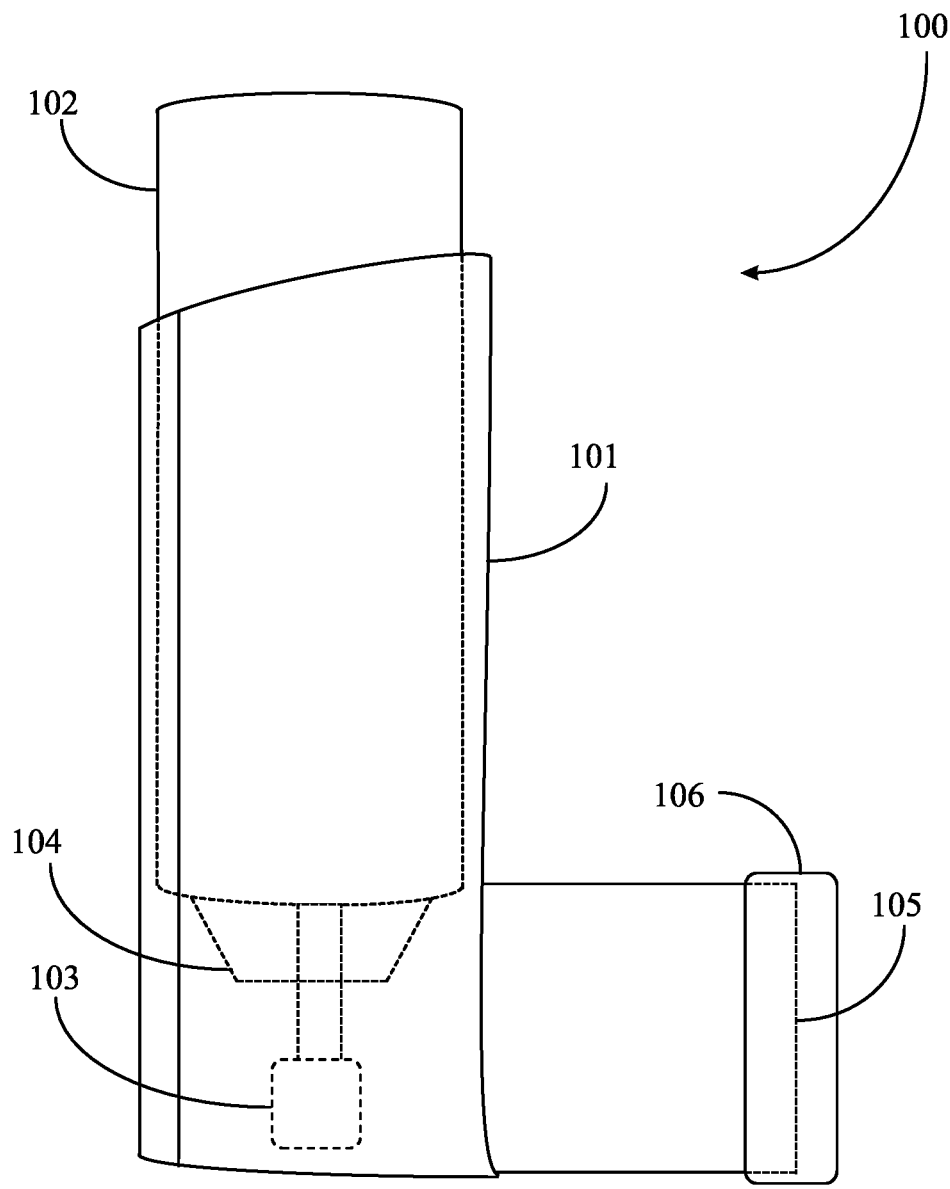
FIG. 1 is a side elevation view of an MDI according to current art.

FIG. 1 is a side elevation view of an emergency medication dispensing device, in this embodiment a metered dose inhaler (MDI) 100 according to current art. MDI 100 is a well-known stock medical device that is adapted to deliver metered doses of one of a variety of aerosol medications such as albuterol medication, for example from a pressurized cartridge containing the medication. MDI 100 depicts basic essential components of an inhaler device of a basic design. MDI 100, also referred to herein as an inhaler device or an inhaler has a generally rigid plastic body 101 that may be a molded rigid plastic or composite body. Body 101 may include a tubular section, which may be a contiguous part of body 101 that may typically be oriented substantially vertically when held for use by a patient inhaling a dose of medication from the device. Body 101 of MDI 100 may include a tubular mouthpiece extension disposed angularly from the vertical tubular section of body 101.

Body 101 may be a molded contiguous form or two body sections that may be assembled in a sealable manner to form a working body 101. It is noted herein that the design of body 101 may be of a different geometric shape than with an annular or tubular design as is the body sections comprising body 101. MDI inhaler 100 includes an aerosol medication canister 102 adapted to contain the medication under pressure. Medication canister 102 is adapted to fit into the substantially vertical section of body 101 in the manner of loading a pressurized medical cartridge for subsequent use. MDI 100 includes an actuator 103 to actuate release of the pressurized medication in a measured amount as an aerosol that a user breathes in through a mouthpiece referenced herein as mouthpiece 105. The actuator 103 is connected to canister 102 by a pressure release stem 104. A cap 106 may be provided to cover mouthpiece 105.

In use of MDI 100, a patient may position the medical device against the lips and operate actuator 103 causing a release of medicine from canister 102 in the form of an aerosol disposed to the inhalant end of body 101 and inhaled by the patient through mouthpiece 105. In typical use, actuator 103 is connected by pressure release stem 104 to the center of the dispensing end of medication canister 102 and is operable by a patient to cause a metered dose of medicine to be dispensed from canister 102 into the lower tubular portion of body 101 for the patient to inhale. It is noted herein that there are numerous designs available for MDIs including those having different angular arrangements between the substantially vertical tube holding the medication canister and the tubular mouthpiece section.

Figure 2:
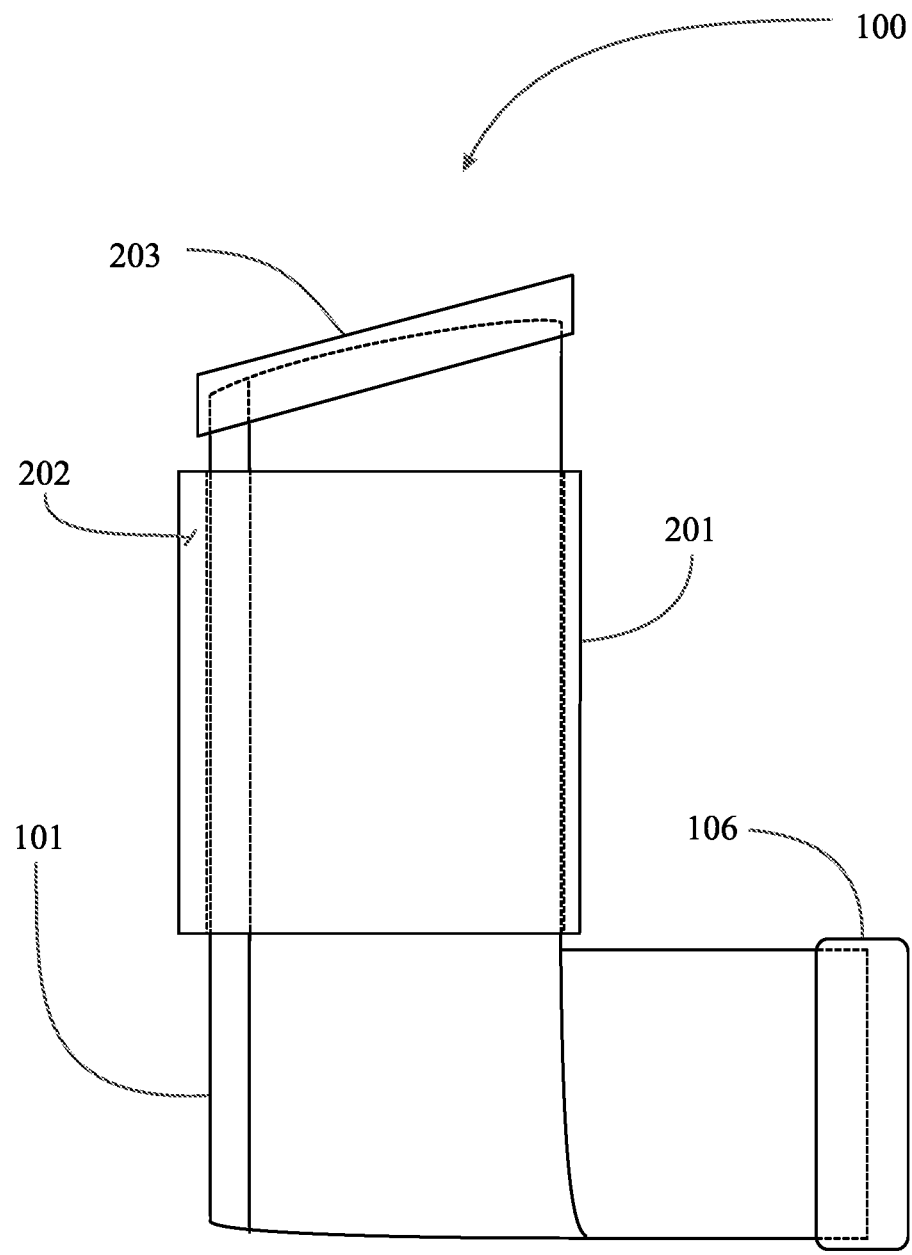
FIG. 2 is a side view of the MDI of FIG. 1 with an electronic material sleeve according to an embodiment of the present invention.

FIG. 2 is a side view of MDI 100 of FIG. 1 adapted with an electronic unit formed as an electronic material sleeve 201 according to an embodiment of the present invention. In this embodiment, MDI 100 is modified with the application of an electronic material sleeve 201 that is adapted to be custom fitted over rigid plastic body 101. In this view, MDI 100 includes a top cap 203 that is not depicted in FIG. 1. Medication canister 102 is not depicted in this view for the purpose of clarity.

Electronic sleeve 201 may be molded in a tubular form from a medical grade elastic material like a silicone rubber or a suitable composite having elasticity. Electronic sleeve 201 has an inside diameter that is uniform in this body and that is smaller than the stock outside diameter of rigid plastic body 101. In a preferred embodiment, the material comprising electronic sleeve 201 is latex free, BPA free, water resistant, and of a medical grade material that can be sterilized. Electronic sleeve 201 may be stretched over and fitted onto the vertical tubular section of rigid plastic body 101 in a manner that is secure due to the elastic tension inherent to the sleeve material. Other than silicone rubber, similar elastic materials like neoprene rubber, or composites thereof may be substituted therefor without departing from the spirit and scope of the present invention.

Electronic sleeve 201 has a wall thickness and an outside diameter wherein the wall thickness is sufficient to enable encapsulation of mini electronic components and circuitry during fabrication of the sleeve. In one embodiment electronic sleeve 100 has a uniform wall thickness. No electronic components or circuitry is depicted in the embodiment but may be presumed present and encapsulated within the wall of electronic sleeve 201. In this view, an electronic unit 202 is depicted defining a preferred general location for disposition of the electronic components of sleeve 201.

Unit 202 may be positioned on the side of MDI 100 away from mouthpiece 105 (FIG. 1) covered in this view by cap 106, which may be a rubber or polymer cap. In one embodiment, electronic sleeve 201 has a thicker wall at the side of electronic unit 202, however this is not required to practice the present invention. In one embodiment, electronic unit 202 may be orientated in other directions relative to the given orientation of MDI 100 without departing from the spirit and scope of the present invention. Electronic unit 202 functions according to design functionality dependent upon the electronic capabilities of the components encapsulated within the sleeve material of electronic sleeve 201. A patient may remove cap 203 to install electronic sleeve 201 over body 101 in a manner as to position the sleeve securely over body 101 down toward the lower tube section of body 101.

Figure 3:
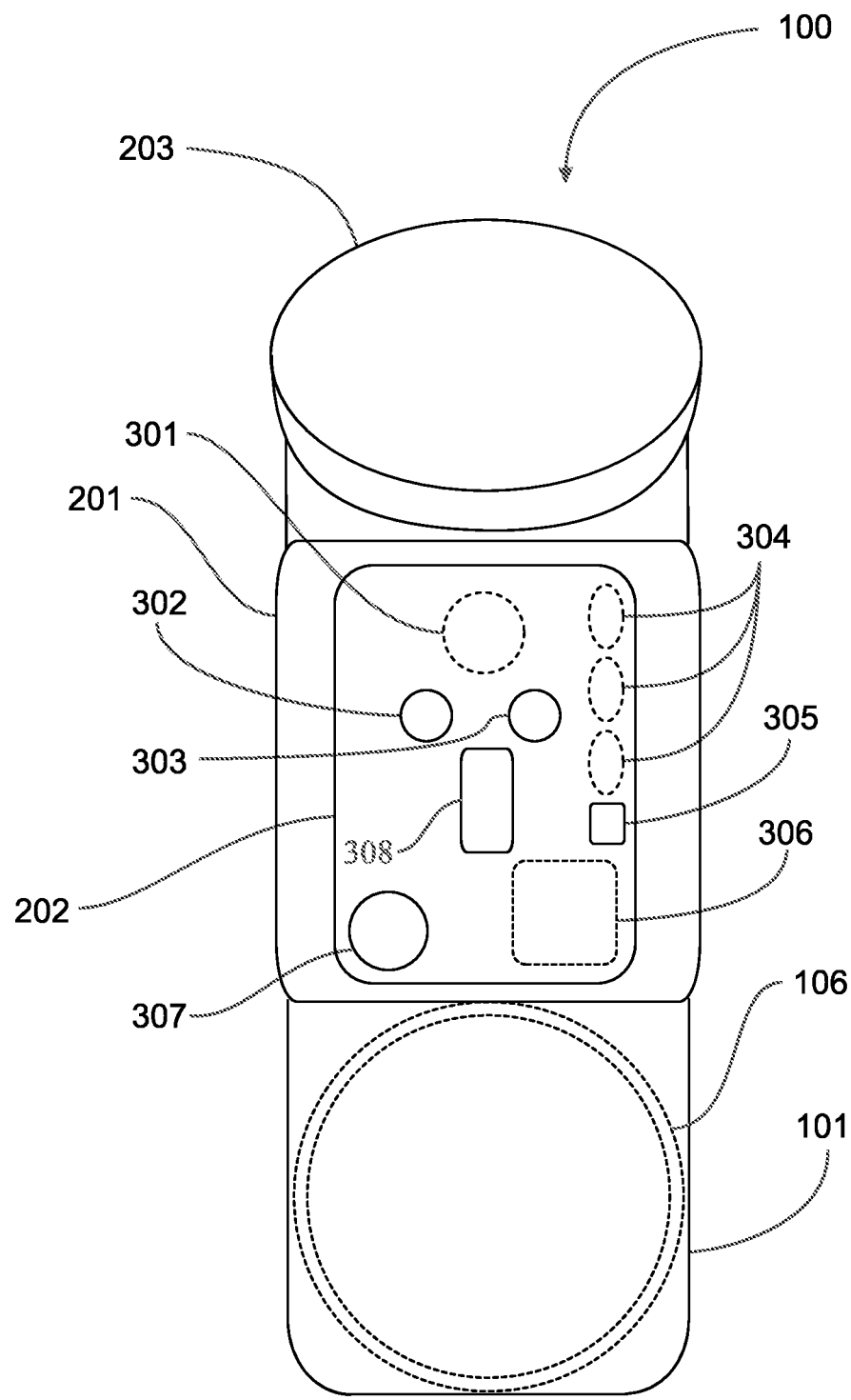
FIG. 3 is a rear elevation view of the MDI and electronic material sleeve of FIG. 2 depicting electronic according to an embodiment of the present invention.

FIG. 3 is a rear elevation view of MDI 100 supporting electronic material sleeve 201 of FIG. 2 depicting electronic according to an embodiment of the present invention. In this embodiment, some of the electronic components in electronic unit 202 are encapsulated within the material of electronic sleeve 201 while other components are visible at the surface of the material. In this embodiment, all the electronic components are positioned away from patient opposite of mouthpiece cap 106.

Electronic unit 202 includes a microprocessor 306 that supports computer aided processing including wireless local area network communication, or a version of Bluetooth™, and or radio frequency identification (RFID), or a similar wireless communications technology. Microprocessor 306 may be powered using one or more rechargeable batteries 304 having trace connections to other power consuming components. One known battery may be a Li ion or similar size rechargeable battery. Electronic unit 202 includes any type of micro universal serial bus (USB) charging port 305 to enable device charging via a supporting computing device or USB charging adapter device. Any known type of electronic charging device may be implemented including any one of USB 2.0, USB 3.0 and USB 3.1, USB Type-A, USB Type-B, USB Type-C, Mini-USB, Micro-USB and Lightning Ports. Alternatively, disposable or rechargeable batteries may be implemented to power the electronic unit 202.

In one embodiment, electronic unit 202 includes an eccentric rotating motor (ERM) 301 to produce vibration upon receiving a signal from an electronic accessory device (not illustrated) detailed later in this specification. An audio speaker 307 is provided within electronic unit 202 for producing a sound alert or notification sound upon receiving a signal from the fob device or, alternatively, in an automated operating mode, when electronic sleeve 201 is more than a preset distance, defined as out of wireless communications range, from the fob or other tracking implement such as a computing appliance, which in this embodiment, may be a smartphone.

In a preferred embodiment, the sound from speaker 307 is audible when the short range signaling and communication may become compromised because of a distance between devices, for example past 9-11, or more meters. In one embodiment, electronic unit 202 includes at least one light emitting diode LED. In this embodiment there are two LEDs provided. One LED may be a strobe light or white light 302 while another LED may be a red light 303 arrayed adjacently and visible from outside of electronic sleeve 201. In this embodiment, only one light may be needed. In one embodiment, lights 302 and 303 may be adapted to flash alternately or in specific patterns to create a visual notification upon receiving a signal from the wirelessly paired fob device (FIG. 4A 400) or other tracking and communication device as previously disclosed. LEDs 302 and 303 may also provide state information relative to charging of electronic sleeve 201. Colors of LEDs may vary such as green and red, green and white, etc. LEDs may be actuated by receipt of a wireless signal and or by an internal state notification command based on internal information or state.

Electronic sleeve 201 may be wirelessly connected to a computer, a cellular phone, and or a fob within range of the active wireless network used. In this embodiment, electronic sleeve 201 includes a patient help or call button 308. Button 308 may be operated by a patient in distress to communicate a signal or message to a network-based emergency service like 911, a medical response team service or a first responder medical service listening for such signals and or messages. In one embodiment, electronic sleeve 201 may include further electronic components that may be added to electronic unit 202 such as a global positioning satellite (GPS) module, a wireless network modem, a subscriber identification module (SIM) or the like. In such an embodiment, electronic sleeve 201 may be located by an RF ID-based fob device or by another Bluetooth enabled device or appliance.

In one embodiment, electronic sleeve 201 may access a network server over a data network to provide a message alert to emergency medical personnel to summon medical help in an emergency like a severe asthma attack or an emergency canister refill requirement. A patient may locate MDI 100 supporting electronic sleeve 201 using a fob device or a Bluetooth enabled appliance as described above. A location signal sent by a fob device (RFID) or by a Bluetooth enabled device may cause ERM 301 to vibrate, and or LEDs 302 and or 303 to flash, and or speaker 307 to emit an audible sound thereby enabling a patient to quickly locate the MDI. In one embodiment, electronic sleeve 201 may be fabricated to custom fit a variety of inhaler body designs having variant geometric body forms, for example tubular forms, rectangular forms, or elliptical forms thereby allowing a patient to customize any stock hand-held inhaler device for wireless communication and tracking. Electronic sleeve 201 may be manufactured from stretchable transparent silicone capable of securely fitting a variety of aftermarket medical devices.

Figure 4A:
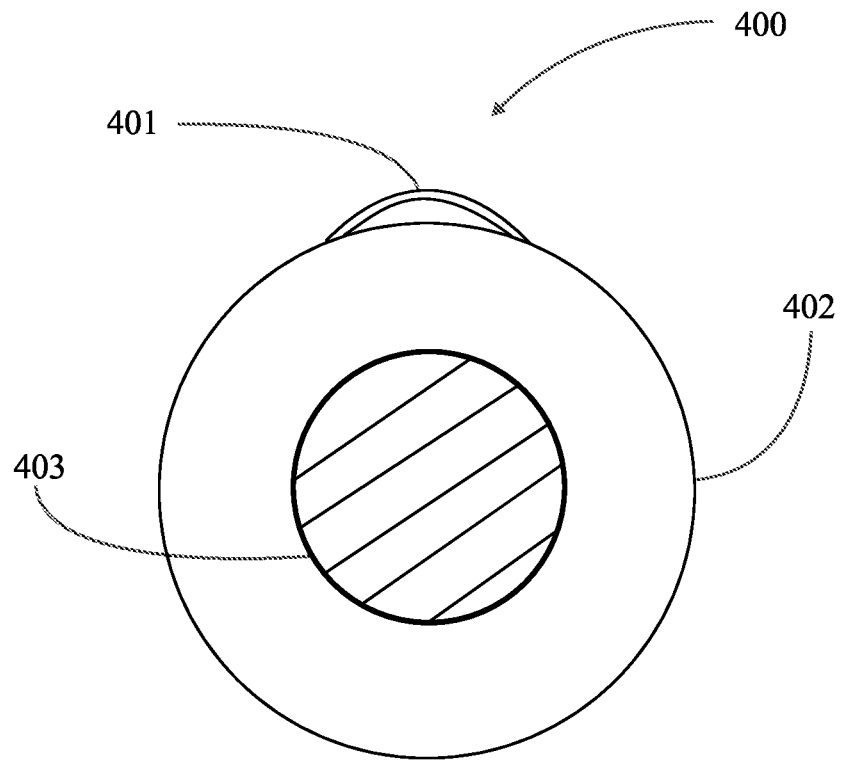
FIG. 4A is an overhead view of a fob device for wireless communication with the electronic material sleeve of FIG. 2.
Figure 4B:
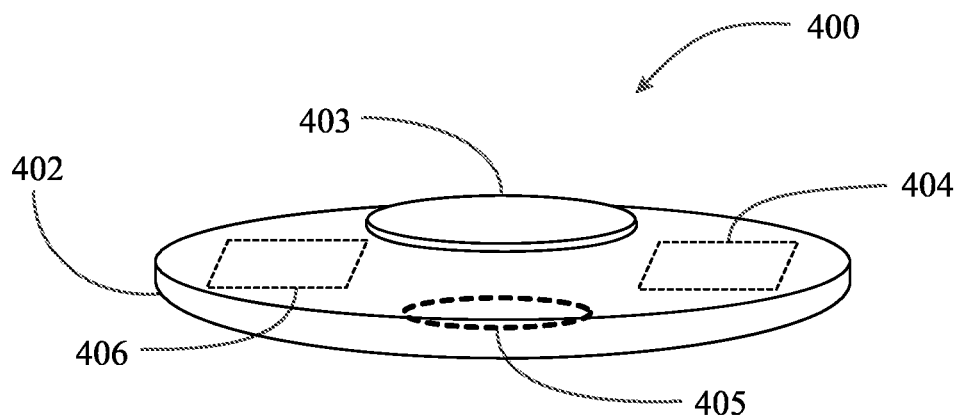
FIG. 4B is a perspective side view of the fob device of FIG. 4A.

FIG. 4A is an overhead view of a fob device 400 for tracking and communication with the electronic material sleeve of FIG. 3. FIG. 4B is a perspective side view of fob device 400 of FIG. 4A. Referring now to FIG. 4A, a fob device 400 is provided and depicted in an overhead view. Fob 400 includes a wire loop 401 for enabling attachment of fob 400 to a lanyard, key ring, or other personal item always kept with the patient. fob device 400 includes a plastic body housing 402 with sufficient volume to house fob electronic components and power source (battery). Fob device 400 includes a find button 403 that a user may depress to send a signal out to MDI 100 customized with electronic sleeve 201 (FIG. 3).

Referring to FIG. 4B, fob device 400 is depicted in a side view further illustrating a communications chip like RFID or a version of Bluetooth 404, and a battery 405 that may be snapped into or otherwise inserted into the bottom of fob device 400. In a preferred embodiment, fob device 400 is provided as a locator device and may employ RFID or any short-range wireless communication such as a version of Bluetooth to locate electronic sleeve 201 (FIG. 3) if it is in range to receive the wireless signal. Fob device 400 may be adapted to work with an electronic sleeve that is exclusively identified to by code ID and may be marketed with the electronic sleeve for a specific brand of inhaler device. Additionally, a specific fob device may be paired with a specific electronic unit 202 in a case where more than one individual in a given area or household operates paired fob/sleeve devices.

In another embodiment the fob device 400 may include additional electronic monitoring components in unit 202 enabling monitoring of rate of respiration and or lung volume during respiration in order to detect a user in stress. Heart rate, blood pressure and other health conditions of a user may also be monitored. In this embodiment, if stress is identified by the fob device, the fob device may activate lights 302, motor 303, or sound emitter 301 to let the user know to keep the medical device near or to use the medical device. In one embodiment fob 400 may have a button 308 enabling alert of emergency medical services.

It is noted herein that electronic sleeve 201 may be provided for other types and brands of medical devices that are portable and required to prevent severe reaction in a patient such as an auto-injector which may inject epinephrine (Epi Pen™), for example.

Figure 5A:
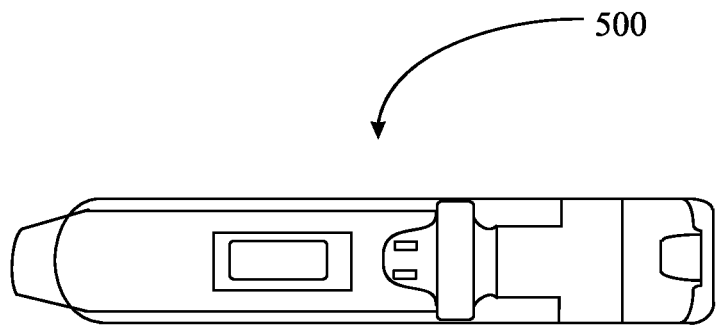
FIG. 5A is an elevation view of a fully assembled auto-injector pen according to current art.
Figure 5B:
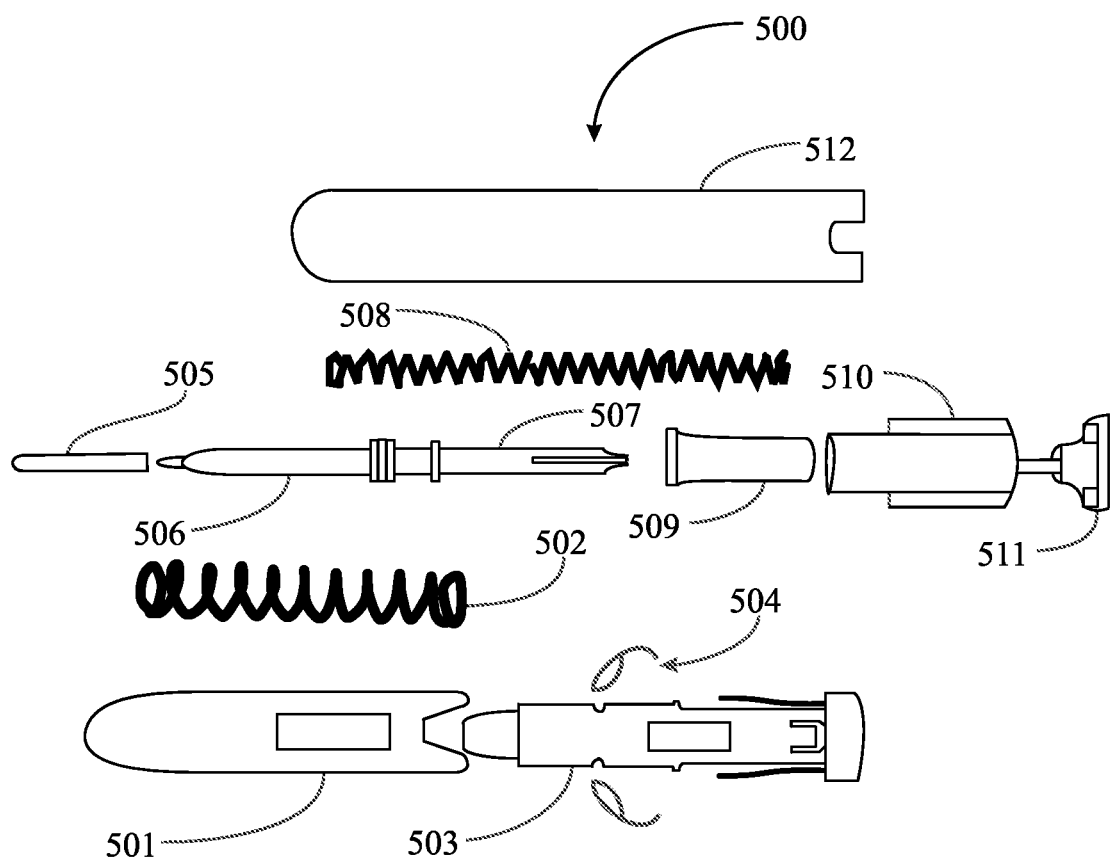
FIG. 5B is an exploded view of the auto-injector pen of FIG. 5A.

FIG. 5A is an elevation view of a fully assembled auto-injector 500 according to current art. FIG. 5B is an exploded view of auto-injector 500 of FIG. 5A. Referring now to FIG. 5A, auto-injector 500 is depicted in an assembled view. Auto-injector is a brand of auto injector devices like device 500 that include other brand names as well. Typically, they all perform the same function of needle injection delivery of cartridge-based epinephrine, which is the primary medicine for countering an anaphylaxis shock event due to an allergic reaction in a patient with one or more serious allergies. Auto-Injector™ 500 is also typically a tubular device. Referring now to FIG. 5B, auto-injector 500 is depicted in a dissembled state for the purpose of revealing the atomic parts of the device. auto-injector 500 includes a housing 512 that protects and encloses all the other parts. auto-injector 500 induces a medicine cartridge 506 and a plunger 507. Cartridge 506 includes a needle for delivering a dose of epinephrine and a needle cover 505 covering the needle for safety purposes. Auto-injector 500 is driven by a drive spring 508 that is stopped at a release collar 509 that fits into a rear body 510. Auto-injector 500 includes a carrier 503 and a shroud 501 that fit concentrically over parts 505, 506, 507, and 509. Carrier 503 includes a pair of control clips 504 that secure a control spring 502. It is noted herein that all the functional parts are assembled in concentric manner within tubular housing 512. A safety cap 511 is provided to cap off the rear of Auto-Injector™ 500. An actuator is internal and is activated when a patient or medical responder presses the needle side of Auto-Injector™ 500 against the skin to trigger a shot injection of a dose of the medication. Although this specification refers to Auto-Injector™ brand of auto-injector device, auto-injector devices of other brands may be substituted therefor.

Figure 6:
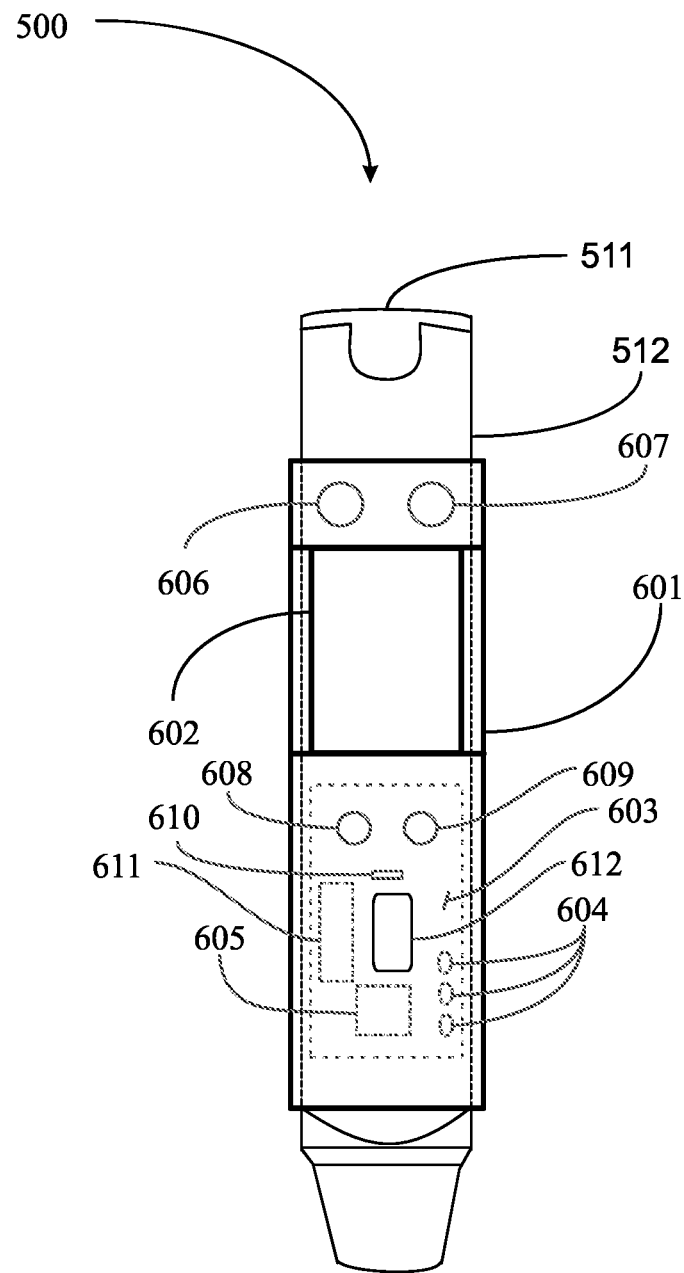
FIG. 6 is an overhead view of the Auto-Injector™ of FIG. 5A with an electronic material sleeve installed according to an embodiment of the present invention.

FIG. 6 is an elevation view of auto-injector 500 of FIG. 5A with an electronic material sleeve 601 installed thereon according to an embodiment of the present invention. Auto-injector 500 is orientated vertically in this view with the needle side down and the cap side up. Auto-injector is modified in this embodiment with an electronic sleeve 601 that is adapted to be custom fitted over the rigid plastic tube housing 512 of auto-injector 500. Electronic sleeve 601 may be analogous in material composition to electronic sleeve 201 described further above. Electronic sleeve 601 may be molded in a tubular form from a medical grade elastic material like a silicone rubber composite. Electronic sleeve 601 is tubular in form in this embodiment and is flexible as well as resilient.

The inside diameter of electronic sleeve 601 is just smaller than the stock outside diameter of an auto-injector like auto-injector 500. In a preferred embodiment, the sleeve material is latex free, BPA free, water resistant, and of a medical grade material that can be sterilized. Electronic sleeve 601 may be stretched over and fitted onto the vertical tubular housing 512 of Auto-Injector™ 500 in a manner that is secure due to the elastic tension inherent to the sleeve. Other than silicone rubber, similar elastic materials like neoprene rubber or composites thereof may be substituted therefor. Electronic sleeve 601 has a wall thickness and an outside diameter wherein the wall thickness is sufficient to encapsulate electronic components and circuitry mostly confined to an electronic unit 603 analogous to electronic unit 202 described further above with reference to electronic sleeve 201 of FIG. 3A. In this view, electronic sleeve 601 has a transparent window 602 that may reside over the instructions typically printed on the outside of housing 512 of auto-injector 500.

In one embodiment, electronic sleeve 601 is fully transparent, in another embodiment, sleeve 601 is opaque except for transparent window 602. A user may operate auto-injector 500 without having to remove electronic sleeve 601. An auto-injector is designed to be used and then thrown away. Electronic skin 601 has a wall thickness that is large enough to host electronic in encapsulated state within the material or in partially encapsulated state where the component is visible and accessible from outside the sleeve. As such, some components are depicted in broken boundary (encapsulated) while some are visible (solid line).

In this embodiment, electronic unit 603 contains at least one LED, in this body two, a red LED 608 and a white LED 609. One LED may be a white light while another LED may be a red light arrayed adjacently and visible from outside the electronic sleeve 601. In one embodiment, LED 608 and or LED 609 may be adapted to flash alternately, or in specific patterns to create a visual notification upon receiving a signal from a wirelessly paired or otherwise connected fob device and or providing information relative to charging state of electronic sleeve 601. Colors of LEDs 608 and 609 may vary such as green and red, green and white, etc. LEDs are actuated by a wireless signal and or by an internal state notification command. In this embodiment, LEDs 608 and 609 are arrayed above a charging port 610 and are disposed toward the needle end of electronic skin 601. Charging port 610 may be a micro-universal serial bus (USB) charge port to enable device charging via a USB supporting device via a USB cable.

Electronic sleeve 601 may include a microprocessor 605 that supports computer aided processing including wireless communication through a version of wireless local area network, for example Bluetooth LE™, and or radio frequency identification (RFID) or a similar wireless communications technology. Microprocessor 605 may be powered using one or more Li ion rechargeable batteries 604 having trace connections to other power consuming components. Microprocessor 605 may store and execute software and/or firmware enabling operation with the fob device, laptop or phone and communication outside of the wireless local area network, either via one of the connected computerized devices or autonomously via communication components within the unit of the sleeve. Microprocessor 605 and Li ion batteries 604 may be disposed toward the needle end of auto-injector 500. In this view, transparent window 602 is disposed over the area of the auto-injector that includes the use instructions printed on the device. In one embodiment, transparent window 602 may extend all the way around the diameter of electronic sleeve 601.

In this embodiment, electronic skin 601 includes an eccentric rotating motor (ERM) 606 to produce vibration upon receiving a signal from an electronic fob accessory device detailed further below, and a sound emitter or audio speaker 607 to produce an amplified audio alert or notification sound upon receiving a signal from the fob device, or when it is detected that the sleeve and fob are separated by more than a specified distance, which may represent a boundary of effective communication within the wireless range. In a preferred embodiment, the sound from speaker 607 is audible past 10 or more meters. A help button 612 may be provided to electronic sleeve 601 that may be operated by a patient in distress to communicate a signal or message to a network-based emergency service like 911, a medical response team service or a first responder medical service listening for such signals and or messages. Electronic sleeve 601 may be wirelessly connected to a computer, a cellular phone, and a fob tracking device within range of an active wireless network.

In one embodiment, electronic sleeve 601 may include further electronic components that may be added to electronic unit 602 such as a global positioning satellite (GPS) module, a wireless network modem, a subscriber identification module (SIM), or the like without departing from the scope of the invention. In such an embodiment, auto-injector 500 with sleeve 601 installed may be located by an RF ID based fob tracking device or by another Bluetooth enabled device or appliance. In one embodiment, electronic sleeve 601 may access a network server over a data network to provide an alert signal or message alert to emergency medical personnel or a medical response service to summon medical help in an emergency like a severe allergic reaction that requires immediate emergency personnel to be dispatched to the scene. In one embodiment, electronic material sleeve 601 may include an up-datable memory device 611 for storing data and firmware. Memory device 611 may be accessed by a patent for the purpose of offloading data, adding data, or synchronizing data using a computing appliance.

A location signal sent by a fob device (RFID) or by a Bluetooth™ enabled device may cause ERM 606 to vibrate, LEDs 608 and or white light or strobe light 609 to flash, and or speaker 607 to emit an audible sound thereby enabling a user to quickly locate auto-injector. Electronic sleeve 601 may be located using a phone or computing appliance running an application or a fob device like fob 404 described further above with respect to FIG. 4A and FIG. 4B. In one embodiment, electronic sleeve 601 may be fabricated to custom fit a variety of auto-injector body diameters thereby allowing a user to customize any auto-injector device for communication and tracking.

A patient may remove electronic sleeve 601 after an injection is achieved and place the sleeve over a second unused auto-injector that replaces the first one. In one embodiment, an auto-injector device may be reused (dependent upon capability) wherein a new cartridge may be inserted therein, and the mechanics of the device may be reset and or reactivated for subsequent use. In this body, a patient may keep electronic sleeve 601 on auto-injector 500 until the patient no longer desires to continue to reuse the same device.

Referring now back to FIG. 4A and FIG. 4B, fob device 400 is adapted as a locator device, primarily, and may employ RFID or a version of Bluetooth™ to locate auto-injector 500 if it is in range to receive the wireless signal. Fob device 400 may be adapted to work with an electronic sleeve that is exclusively identified by code ID and may be marketed with the electronic sleeve for any specific brand of auto-injector device. In one embodiment, two electronic sleeves like sleeve 601 may be provided with a double pack of auto-injectors one sleeve already custom fitted to each device wherein a patient may first charge one electronic sleeve for one auto-injector to locate the pack when it is in range. It is noted herein that an auto-injector is good for about 18 months in terms of medicine expiration. Therefore, when batteries become low, electronic sleeve 601 may report that to a patient by a visual or wirelessly transmitted signal (dependent on capability) informing the patient of a need to recharge the electronic sleeve though the auto-injector has not yet been used. In this embodiment the same type of signaling by sleeve 601 may be used to indicate the medication may be expired.

Figure 7:
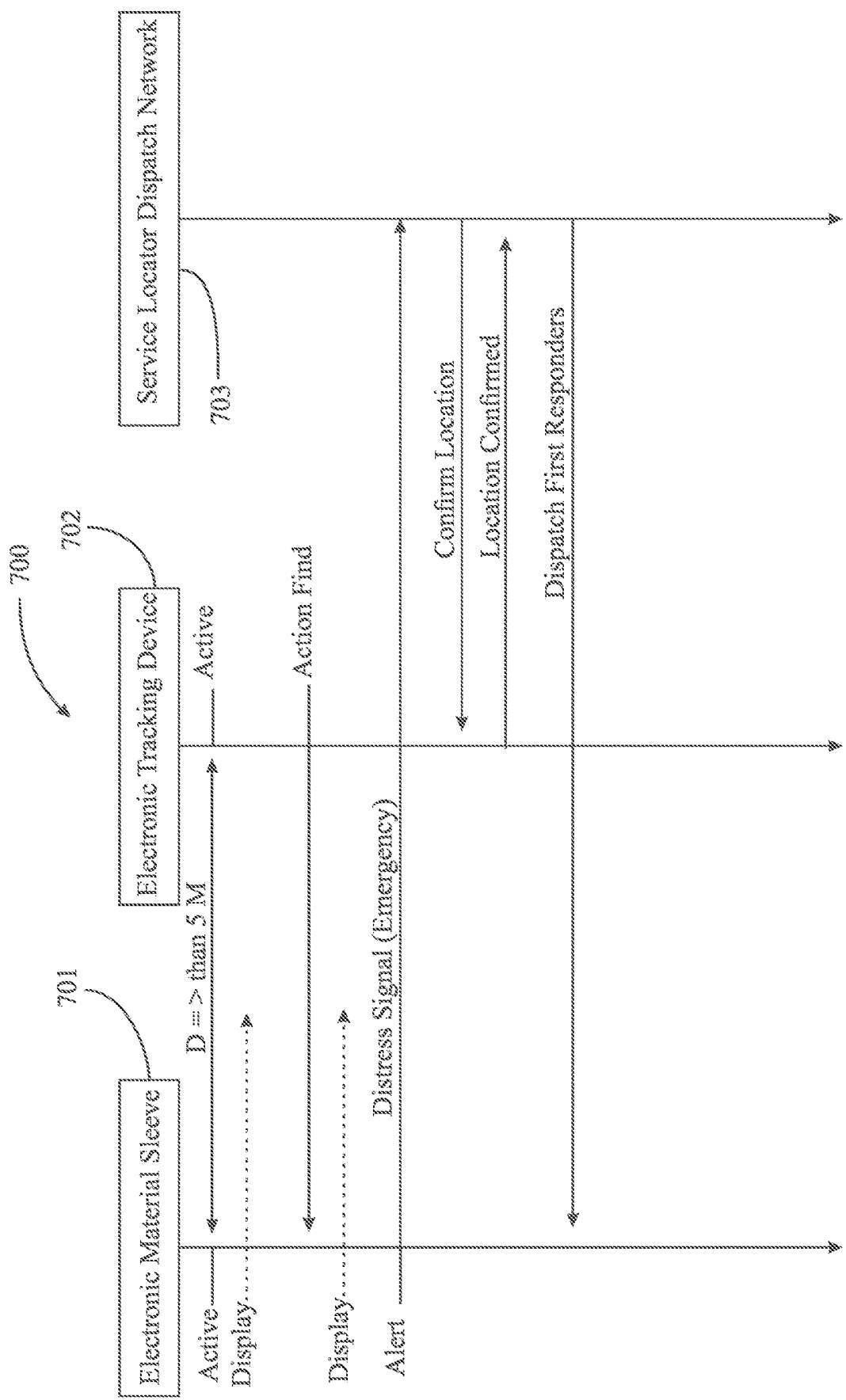
FIG. 7 is a sequence chart depicting sequences of interaction for locating an electronic material sleeve and for reporting an emergency alert requiring medical responders.

FIG. 7 is a sequence chart 700 depicting sequences of interaction for locating an electronic material sleeve and for reporting an emergency alert requiring medical responders. Chart 700 represents an electronic material sleeve 701 which may be analogous to electronic sleeve 201 of FIG. 3A and to electronic sleeve 601 of FIG. 6. Electronic sleeve 701 is tracked using an electronic tracking device 702, which may be analogous to fob 400 of FIG. 4A, or which may be analogous to a patient's mobile cellular phone, or other Internet capable computing device. Chart 700 represents a network-based domain 703, which may be analogous to any cooperating emergency response location and dispatch service.

In a preferred embodiment, electronic tracking device 702 is in an active state and paired with or otherwise wirelessly connected to electronic material sleeve 701, which is also in a charged and active state. In one embodiment, an automated notification mode exists for a situation where a distance D between the electronic sleeve and tracking device becomes greater than a specified distance, which may represent a distance reflecting a boundary or near boundary of wireless service range. In auto mode, when the electronic sleeve 701 and the tracking device 702 are separated at near or beyond wireless range (whether Bluetooth, or RF-ID), an internal state notification signal may be executed locally on the electronic sleeve causing the electronic sleeve 701 to display flashing lights, vibration, and to sound an audio alert. A patient may be enabled to set distance for the devices short of losing wireless contact with electronic sleeve 701.

In another embodiment, a patient may execute an intended action by pressing a find button on a fob or by selecting a find option from a tracking software (SW) application executed and running on a tracking device where the tracking device is a cellular phone or a laptop computing device. Manually executing find may send a wireless signal (command) to electronic sleeve 701 to display in the same visual and audio manner as in auto mode by flashing lights, emitting audio, and vibrating. In one embodiment, a patient may program electronic sleeve 701 to only display light, only display sound, only display vibrating or to display a combination of those or all of those.

In one embodiment, electronic sleeve 701 includes a network modem and GPS location components required to access a wide area network (WAN) like the Internet network for example or a local emergency network. In one embodiment, electronic sleeve 701 includes a GPS/GPRS module, a user operable help button (network access), and an internal memory device or a secure digital (SD) memory card that fits into a card slot partially encapsulated within a wall of the electronic material sleeve 701, the memory device or card containing data about the patient including medical information, emergency service contact information, and contact information of family and friends. GPS/GPRS may enable a patient to locate electronic sleeve 701 (MDI sleeve, Auto-Injector™ sleeve) remotely using a network connected device like a cellular phone or laptop computer connected to the network. A user operable help button integrated into the electronic sleeve like help buttons 308 (MDI sleeve) or 612 (auto-injector sleeve) enable a patient in distress to send an alert by depressing the help button, the alert received by service locator dispatch point 703. Service 703 may offer a service that locates a response facility most local to the patient and may dispatch one or more individuals to the distress scene. Service 703 may use GPS/GPRS to locate that patient by locating the patient's tracking device (if GPS enabled) in the sleeve or alternatively, in the fob device. Once confirmed, responders may be dispatched to the location of the patient. In a variant of this embodiment, the service may locate the patient electronic sleeve (if GPS enabled). Tracking device 702 may use BT/RFID to locate electronic sleeve 701 if the sleeve is within range.

A patient or agent thereof may access memory on electronic sleeve 701 through a micro-USB port connection to a computing device in one embodiment. A patient may store and update patient data, or medicine availability data, or store other important data like medicine canister type and availability data, use state of the inhaler device (use counter), or other data deemed important to store in the electronic sleeve. Firmware (FW) updates may also be provided to update or replace FW on a microprocessor and other processing chip components of an electronic sleeve like sleeves 201 and 601 previously described. Tracking device 702 may be a fob device and may employ Bluetooth/RFID executed by depressing the fob button (find).

In one embodiment, tracking device 702 may be a fob device having RF and short-range wireless (Bluetooth™) transmitters wherein electronic sleeve 701 has the complimentary RF (tag) and short-range wireless (Bluetooth™) receivers provided within. In one embodiment, a patient or agent thereof may leverage USB capability on an electronic sleeve through a USB connection and using a SW application executed and running on a mobile device like a cellular phone or Laptop, and may configure the alert notification features of the electronic sleeve, selecting which features or combination of features sound, vibration, and or visible light, to activate and which if any to moot on the electronic sleeve.

Figure 8:
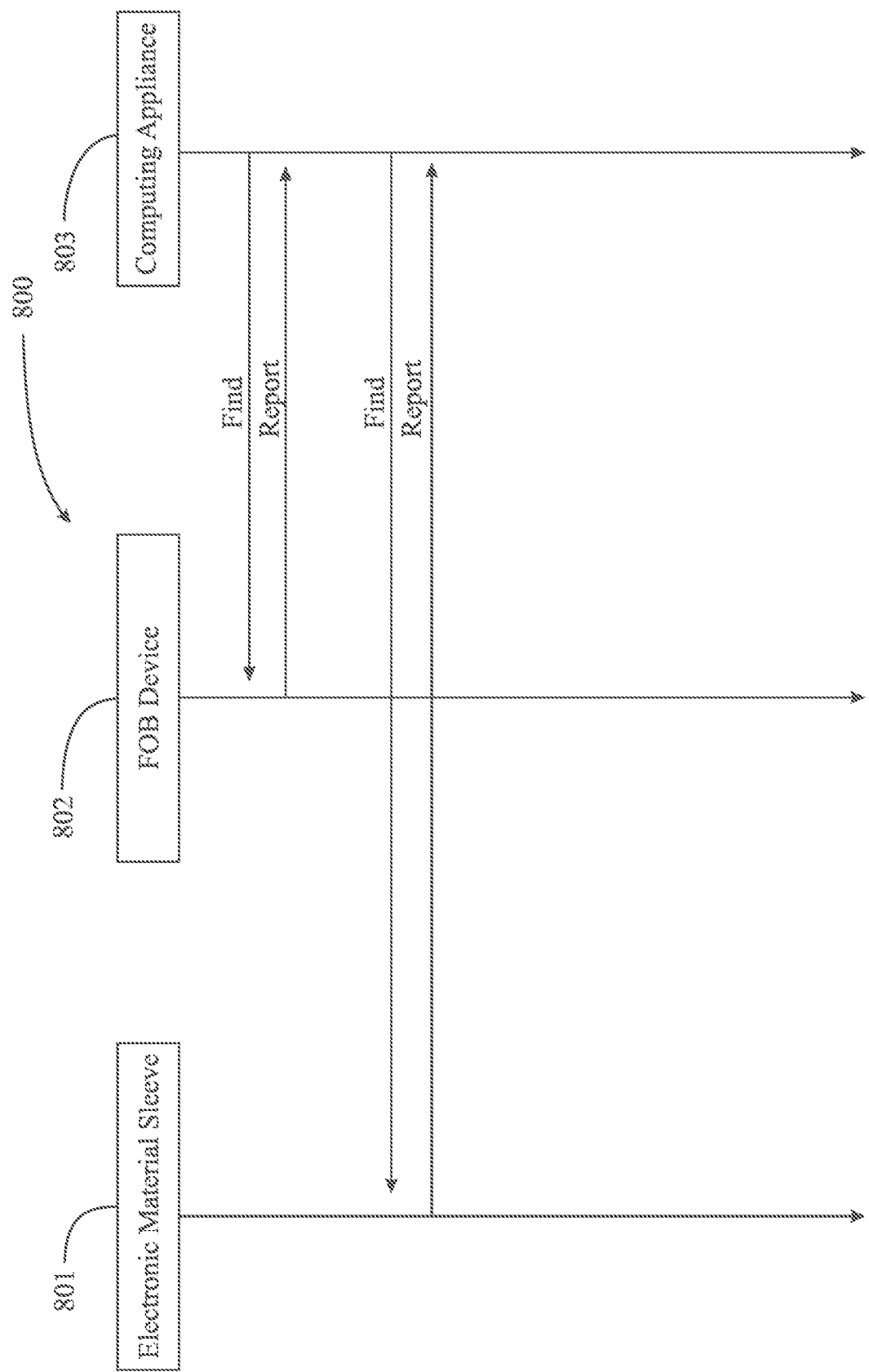
FIG. 8 is a sequence chart depicting sequences of interaction for finding an electronic material sleeve and for finding an associated fob device.

FIG. 8 is a sequence chart 800 depicting sequences of interaction for finding an electronic material sleeve and for finding an associated fob device using a computing appliance. Chart 800 represents interaction between an electronic material sleeve 801, a fob device 802, and a computing appliance 803. Computing appliance 803 may be a patient's mobile cellular phone, laptop computer, or other appliance capable of wireless communication. In this embodiment, both electronic sleeve 801 and fob 802 are Bluetooth™ capable and can communicate with computing appliance 803. In one embodiment, commuting appliance includes a small software (SW) application that provides a user interface having selective options for connecting wirelessly to each device and options for pinging or signaling those devices to at least display sound, light, and vibration sufficient to reveal location in a local sense.

For example, a patient may use computing appliance 803 to find fob device 802 by selecting "Find fob" in an application user interface (UI) executed from memory on the computing appliance. fob 802 may respond to a request sent by sounding, flashing, and vibrating such that a patient operating the computing appliance may notice the location by seeing, hearing, and feeling. Similarly, a patient may use computing appliance 803 to find or locate electronic sleeve 801 in the same fashion. Electronic sleeve 801 may, in one embodiment, be adapted under programed conditions to access a network access point on a network through a network modem and report the current GPS location thereof for emergency response purposes or simply so it may be found by a patient who may have left it or lost it somewhere between uses. Programming electronic sleeve 801 may include loading data onto a memory provided within the sleeve and available to the microprocessor including contact information for family, friends, doctors, or emergency dispatch services.

The electronic material sleeve 801, through both passive and active alert systems (RFID and Bluetooth™), may greatly improve the chance that the medication required by a patient will be immediately available to the patient whenever and wherever needed. The inhaler skin alert/find processes use the fob (token, charm, pendant, etc.) which can easily be carried everyday on a user's body via bracelet, necklace or other wearable device. Alternatively, the device may be attached or integrated with a user's phone, keys, or wallet.

In one embodiment, the user may activate the fob device or other computerized device like a phone or laptop to signal a find function for the emergency medication dispensing device, wherein anyone or more of the LEDs, sound emitters, and ERM of an associated electronic sleeve may activate. The microprocessor software/firmware in the sleeve unit 603 may monitor for medication usage after activation of the sleeve, via anyone of a motion sensor or sensing if medication has been dispensed. If the microprocessor fails to detect usage of the medication in the device, or the user does not deactivate the sleeve device alerts, via the fob or other computerized device an emergency message may be sent to an emergency medical facility to make contact with the user and/or send emergency medical professionals, for example via ambulance or fire department to a premises where the user may be located.

Figure 9:
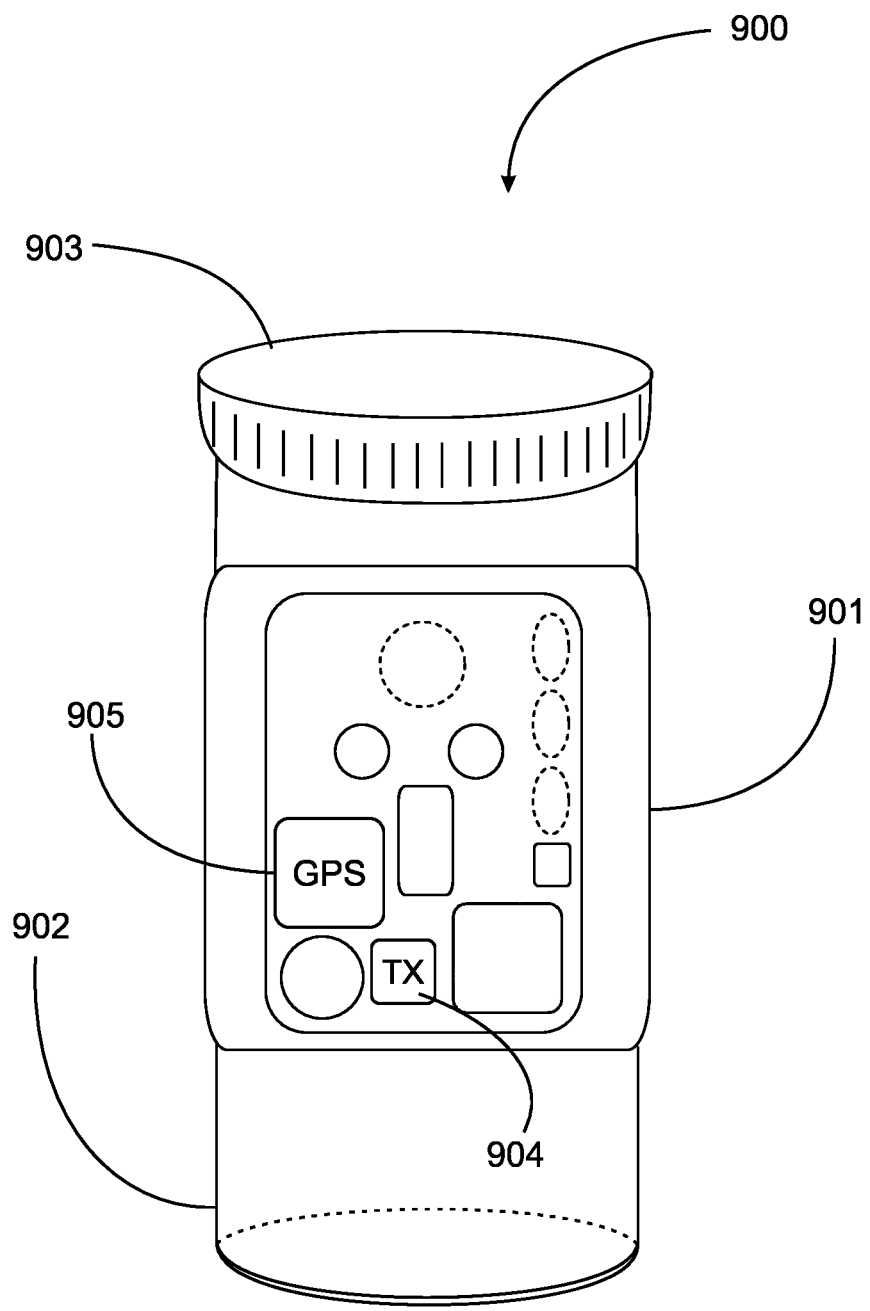
FIG. 9 is an elevation view of the electronic sleeve incorporated with a medicine dispenser.

FIG. 9 shows another embodiment where a medicine dispenser assembly 900 includes electronic sleeve 901, which is integrated with dispenser body 902. In this embodiment sleeve 901 may be permanently affixed to medicine dispenser body 902 or may be removably attached to body 902. In one embodiment, the sleeve device, or electronic unit may be embedded between walls within a dual wall construction of dispenser body 902.

Sleeve 901 includes all the components included from FIG. 3 above. This includes the microprocessor and all of its functionality listed above, the charging port, the electronic rotating motor (ERM), the audio speaker, and the three lights having different colors red, blue and white, although any colors may be used. The patient help and call button are also included in this embodiment which may be connected to a cellular or satellite network. Any electronic components required for the cellular or satellite communication are included in this embodiment. A SIM card may be included, and the sleeve is fully capable of working with the FOB device as shown in FIG. 4.

This embodiment includes dedicated elements including a global positioning system (GPS) transceiver 905. Alternatively, the GPS system may be incorporated within the functionality of software in the microprocessor. A dedicated transceiver 904 may also be included which enables three separate communication capabilities. These include satellite communication, cellular network communication, WiFi and short-range wireless communication such as Bluetooth™. The transceiver may communicate with an associated application on a smartphone, which communicates with a server, or enables communication directly with a server. In this embodiment, the transceiver provides communication between the microprocessor, GPS, smartphone application (discussed below) and a remote server.

Figure 10A:
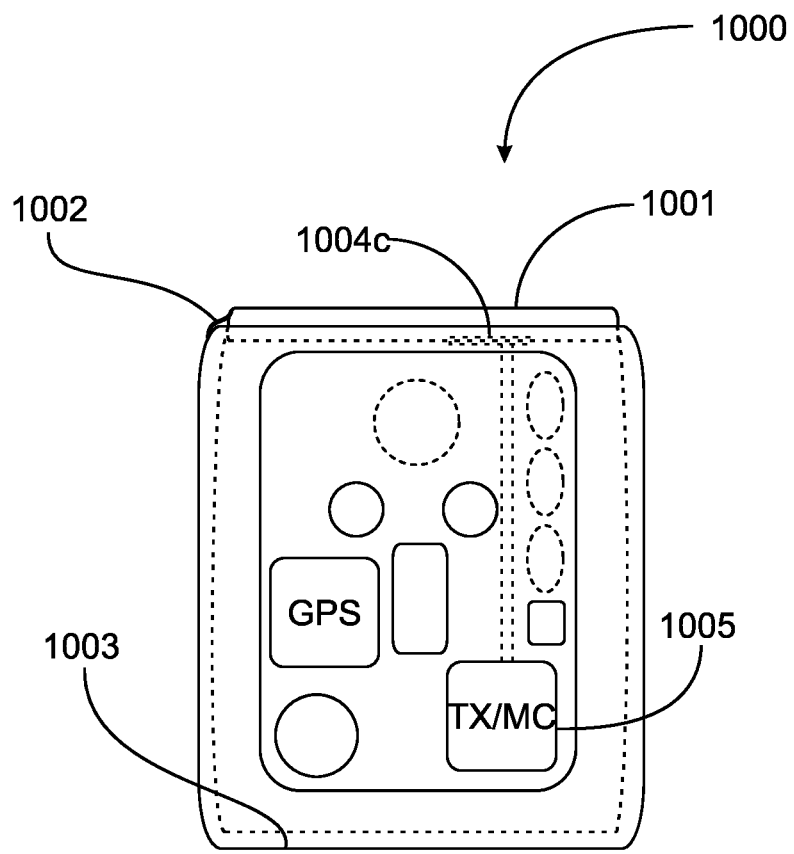
FIG. 10A is an elevation view of the electronic sleeve with additional components.
Figure 10B:
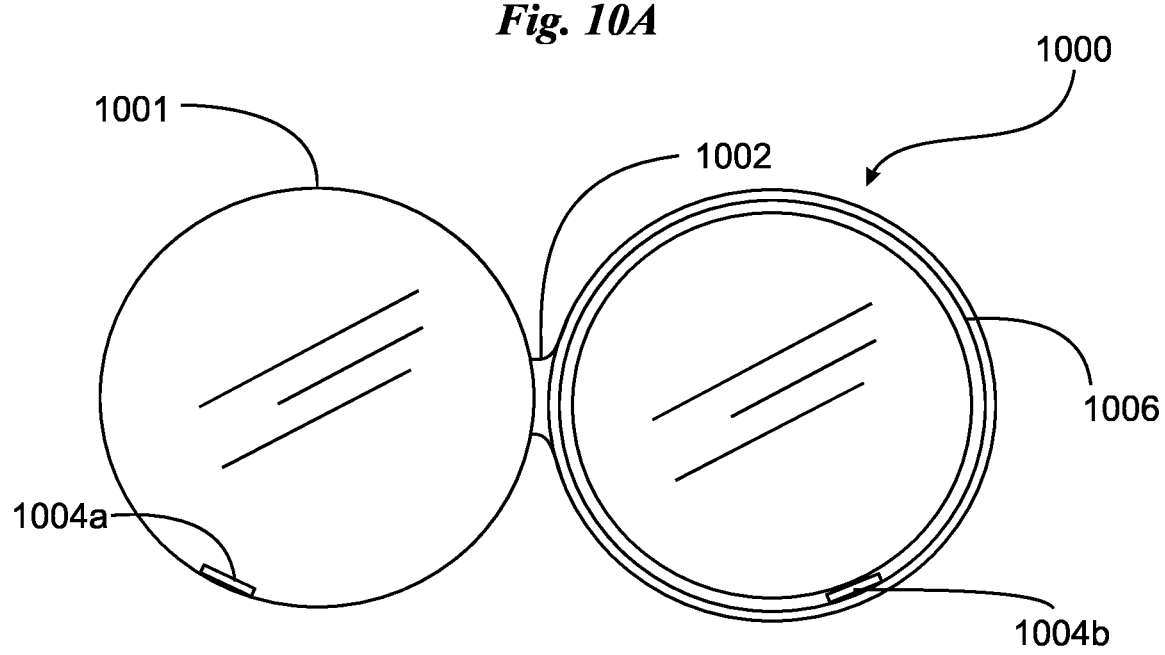
FIG. 10B is a closeup view of a special cap used on the medication dispenser.

Emergency medication dispenser assembly 900 is enabled to accept emergency medications, for example, medications that must be taken within a short time of having an acute attack like nitroglycerine for heart attacks and angina or Narcan™ to assist in overdose emergencies. Emergency medication dispenser assembly 900 may come in varying sizes to contain a wide array of medications. One of the main purposes of using a dispenser like dispenser assembly 900 is an ability to locate emergency medication or emergency medication dispensing devices during a life-threatening event for a user or patient. In this embodiment a user may activate a fob worn on their body as a necklace or wristband or on some other area on their body. The fob may be pushed or activated to locate the sleeve device 901 that is attached around or formed to the medication dispenser 900. Cap 903 may be opened providing access to an inner volume of the medicine dispenser assembly 900. In one embodiment, cap 903 may be a child safety cap that must be pushed and turned to open it or operate child safety capabilities in a different manner. FIGS. 10A and 10B show the form and function of a safety cap assembly 1000.

Safety cap assembly 1000 includes a cap 1001 and a ring adapter 1006. Cap 1001 is attached to ring adapter 1006 by an attachment tether 1002. As can be seen in FIG. 10B cap 1001 includes a contact 1004a and ring adapter 1006 includes a contact 1004b. The two contacts are positioned in the cap and the ring adapter in a manner to create a closed circuit. When the cap 1001 folds over and is snapped into place and closes within the ring adapter 1006 the two contacts 1004a and 1004b become adjacent. A contact receiving pad 1004c is at a location at the top of the dispenser body above the electronic sleeve to be adjacent to contact 1004b thus completing a closed circuit. The closed circuit indicates that the cap is closed. When one opens the cap 101 or contact 1004 B becomes separated from contact receiver pad 1004 C the circuit is broken meaning someone is opening the medicine dispenser assembly 900. The microprocessor/transceiver 1005 may record whether the circuit is closed or open, and alert a user via audible, visual or motion vibration as discussed above. In this embodiment an alert may be sent to an application on a phone allowing the user to be notified when the medicine dispenser assembly is open.

In this manner a user knows if someone is opening their medicine dispenser without their knowledge. This is an advantage to users that keep very valuable medicines like opioids, expensive cancer medicines and other painkillers or medicines that are desirable by others or are particularly costly as is known in the US today.

Figure 11A:
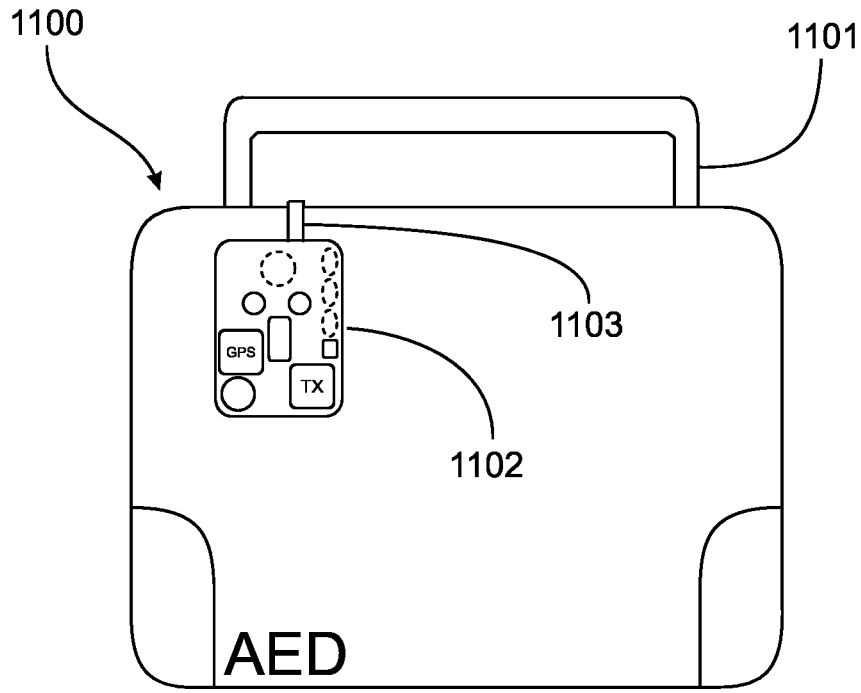
FIG. 11A is an example of the electronic sleeve unit installed on an AED device.
Figure 11B:
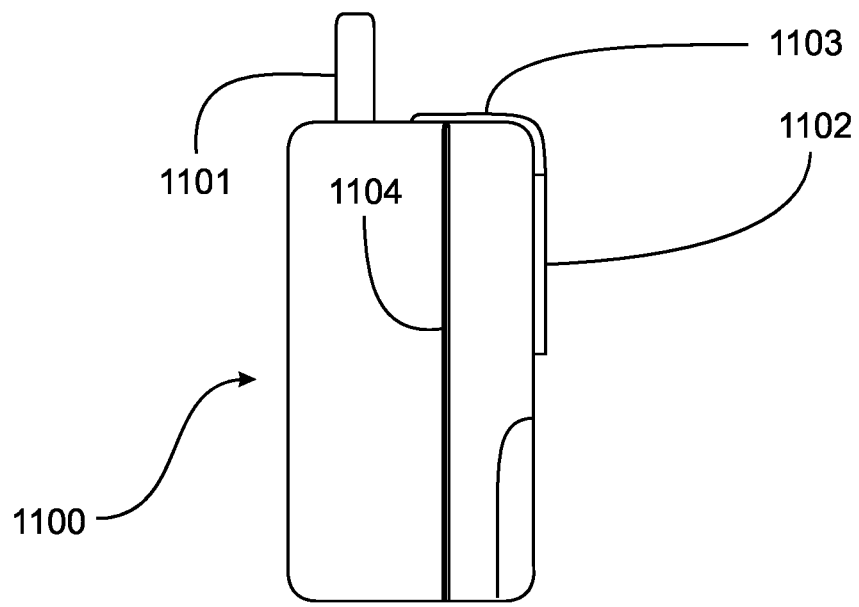
FIG. 11B depicts operation of an activation alert system installed on the AED device.

FIGS. 11A and 11B show an example of the electronic unit in the form of an electronic patch 1102 assembled on an automated external defibrillator (AED) case 1100. Electronic patch 1102 includes all of the electronic components introduced in FIG. 9. The components are also embedded within the material introduced, above, or may be a molded contiguous form or two body sections that may be assembled in a sealable manner to form a working body with the electronic components within, as introduced and described in the above figures. Electronic patch 1102 may be affixed to the AED case 1100 with adhesive of a grade to semi-permanently adhere the patch to the AED case.

Electronic patch 1102 is attached permanently or removably near seam 1104 which defines an opening between two halves of the AED case 1100 while not interfering with handle 1101. Contact strip 1103 extends from the electronic patch 1102 across seam 1104 in this manner, when the AED case is opened in an emergency and the contact strip 1103 is broken or becomes disconnected across the seam an alert is sent to an associated smartphone by the transceiver to alert the user or sends an alert to the server and smartphone connection to be explained further below. The electronic patch may also sound an alert by its alert mechanisms including the LED lights audio speaker, and vibrating motor. In one embodiment, the server may alert emergency personnel such as ambulance police or another medical team to assist at the site where the AED machine is located as determined by the GPS.

In the above embodiments, the emergency medication dispensers may be any of a list including a cylinder with adjustable regulator, an epi pen, a metered spray bottle, a nasal spray bottle, an oral inhaling device, a syringe and a medication dispenser having an inner volume and a removable cap, the medication dispenser integrated with an electronic unit of the electronic unit as shown in FIGS. 10A and 10B. The emergency medication dispensed by said dispensers may be any of a list including oxygen, epinephrine, nitroglycerine, diphenhydramine, albuterol/salbutamol, aspirin, glucose, atropine, hydrocortisone, morphine or nitrous oxide, naloxone, lorazepam or midazolam and flumazenil. The emergency medical equipment may be any from a list including at least an automated external defibrillator (AED), a rescue suction device, an oxygen mask, electrosurgical units and a portable ventilator. The lists presented here are not exhaustive and may include any drug dispenser or device one may require in a medical emergency. A medical emergency may be defined as an immediate life threatening condition of a user or life threatening condition that may be imminent.

Figure 12:
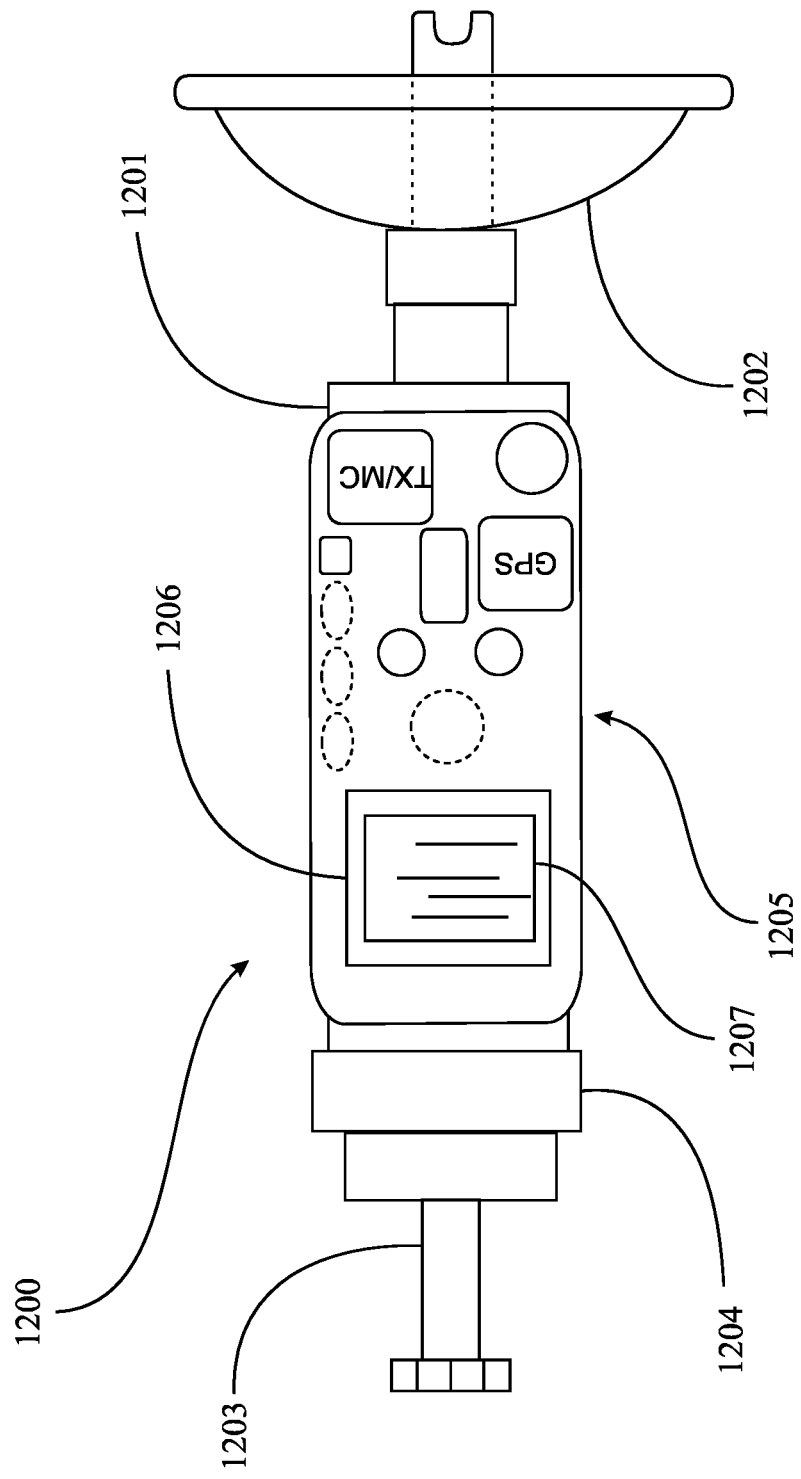
FIG. 12 is an embodiment showing the electronic sleeve on a rescue suction device.

FIG. 12 depicts an electronic sleeve 1205 on rescue suction device 1200. Suction device 1200 also includes A plunger 12/03 a ceiling cap 1204 a cut out window 1207 and enabling a user to read use instructions of the device. A body 1201 is hermetically sealed except to provide suction at mask 1202. In this embodiment the rescue suction device must be found in an emergency of an individual choking, very quickly. When an airway is obstructed in a human being it must be cleared within 4 minutes in order to avoid a vegetative state or death. In this embodiment, the fob device may be used to activate the electronic sleeve 1205 to alert to the presence and location of this device within a household or business. The fob device may be worn on the body of a person or affixed to a specific location within a home or business such as the refrigerator or in an area where people and children often consume food and beverages. Additionally, a smartphone may be connected to the electronic sleeve 1205 mounted to the rescue suction device 1205 in order to activate alerts on the electronic sleeve to quickly locate the device in an emergency.

Figure 13:
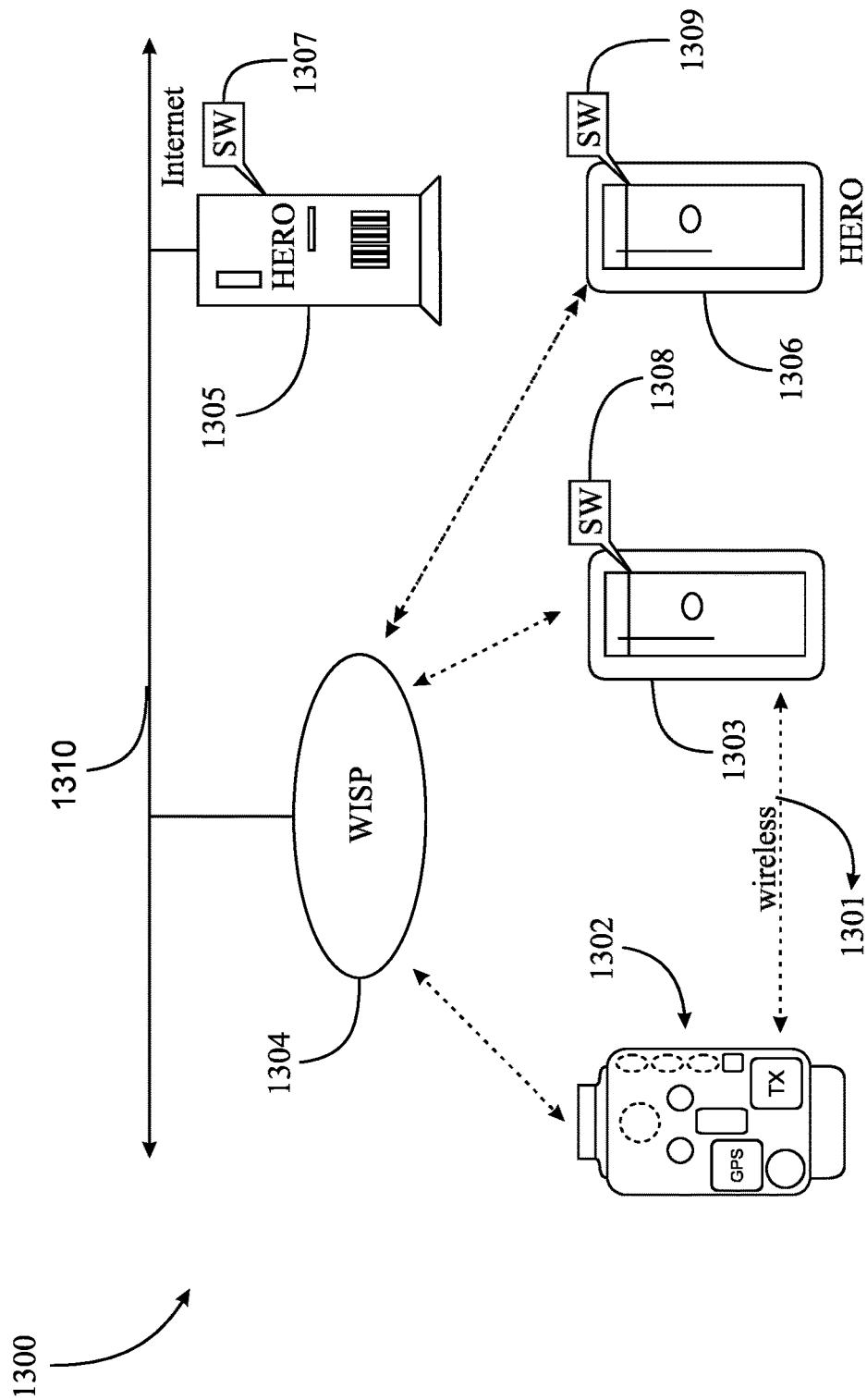
FIG. 13 shows an example schematic of a communication network with electronic components and application on a computerized device of the present invention.

FIG. 13 shows a communication schematic 1300 wherein the Internet is represented by Internet backbone 1310 having a connection to wireless Internet service provider (WISP) 1304. An Internet server 1305 is connected to the Internet as includes software 1307 installed and executing from a computer-readable medium at the server. Smartphone 1306 is also connected to the WISP via cellular or satellite networks and shows an instance of the software 1309 installed providing a help, emergency, rescue others (HERO) application. 1301 depicts a short-range wireless connection, for example (Bluetooth™), between the smartphone 1303 and the transceiver of the electronic sleeve 1302 in this embodiment. In this embodiment 1302 may be any type of electronic sleeve or patch associated with any type of emergency medicine or emergency device. The transceiver 1302 may also have a direct connection to the wireless Internet service provider, the connections shown by the bidirectional dotted lines. In this manner the electronic sleeve 1302 may connect with smartphone 1303 via Bluetooth™ or connect directly to the Internet server 1305 which may facilitate direct communication between the two smartphones 1303 and 1306 and/or electronic sleeve transceiver and smartphone 1306 which is outside of the short-range wireless network.

In this embodiment the HERO application is installed on smartphone 1303 and smartphone 1306. The application provides constant GPS coordinates to Internet server 1305. In this embodiment, if a user having either smartphone has an emergency in need of emergency medication or an emergency device, an alert can be sent out to all smartphones in the area, yet outside of the short range wireless environment of 1301, like smartphone 1306, so other users having the HERO application on their phone can be directed to, and aid users during an emergency who may not have an adequate supply of medication or a correct medical device readily available.

In one embodiment, each user who downloads the HERO application to their smartphone registers their emergency medication and the emergency devices they have available locally. Each registration number may be associated with an electronic sleeve or electronic patch attached to that emergency medicine or emergency device.

Figure 14:
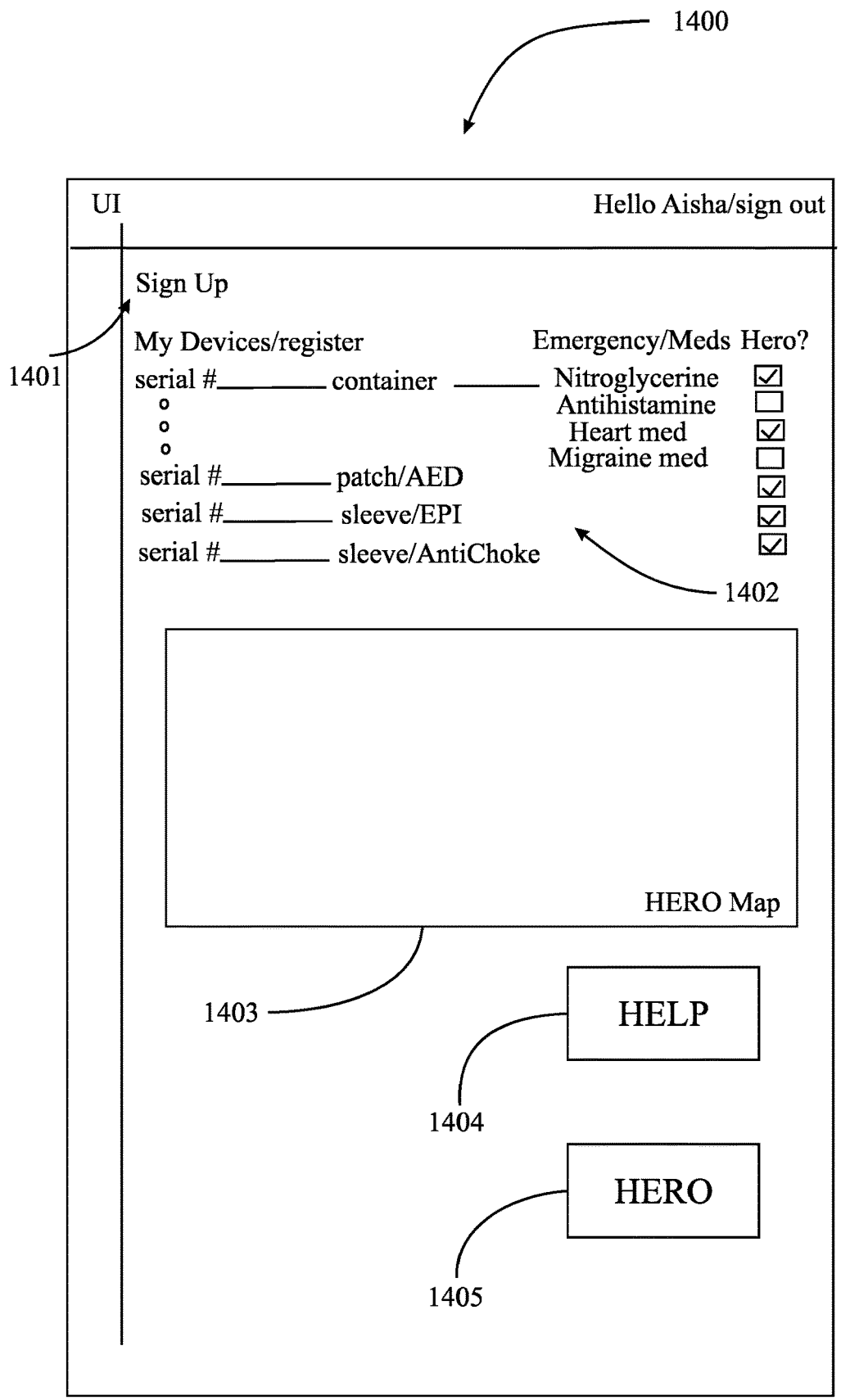
FIG. 14 is an example of a user interface of the application on the computerized device.

FIG. 14 is an example of a user interface 1400 of the hero application on each smartphone. The smartphone may be any computerized appliance including tablets laptops or a desktop computer. The inventors of the present invention also envision a dedicated computerized hardware device hosting the HERO software enabling designated emergency personnel having a supply of emergency medicines and emergency medical devices to assist the general public. In this embodiment, emergency personnel may be working in large stadiums or large concerts holding 10s or 100s of thousands of people where emergency medicines and emergency devices will be required. With the hero application and GPS installed on the smartphones an individual in an emergency situation need not wait until emergency personnel transport them to a medical tent or medical facility to get the emergency medicine or equipment that they require. Emergency medicine and equipment may be implemented on-site saving precious minutes and saving lives.

User interface 1400 is presented to the user after download from the server 1305. A signup link 1401 is provided enabling a user to upload their personal identification information, address, contact info and their medical conditions. In one embodiment the software and server may recognize particularly severe medical conditions of individuals, or individuals that have a medical condition that renders them more prone to suffer a medical emergency, such as small children (choking) heart conditions, asthma sufferers and drug addiction. A user may activate an electronic sleeve or electronic patch to be associated with a specific medication or emergency device.

Section 1402 is provided in the user interface 1400 where registration or serial numbers are assigned to electronic sleeves or electronic units associated with (one each) to specific containers, medicine dispensers, AED's, epi pens, inhalers, etc. In another embodiment, registration or serial numbers are assigned at the time of manufacture of the electronic sleeves and patches and are recorded upon connection between the electronic sleeves/patches to the HERO application on the smartphones.

In this embodiment a medical professional or a member of the public may register their emergency medicines and emergency medical equipment and associate them, one each, to a sleeve or patch that encases or is mounted to the medicine, medicine dispenser, or emergency device. The user, medical professional or member of the public may be alerted to become a hero and help another user by having the HERO application on their phone as well. Any user having the HERO application installed on their smartphone may be an emergency aid receiver as well as be a hero and assist another user in an emergency.

All data associated with the HERO application is stored in a database (not shown) at Internet server 1305. The server may track the location of the individual smartphones, which is a general indication of where a user having an emergency or a potential hero willing to assist another is located. The server also tracks location, via GPS of all registered electronic sleeves and patches associated with emergency medicines and emergency medical equipment.

In one embodiment, a map 1403 may be presented, along with a HELP link 1404 and a HERO link 1405 in the user interface 1400. For example, if an individual has an emergency and needs their epi pen, they may use a fob to activate an electronic sleeve, like sleeve 601 of FIG. 6 associated with and mounted on their epi pen. Unfortunately, the epi pen is used or non-operational, so they activate the HELP link on their HERO application installed on their smartphone 1303. A user having smartphone 1306 may be determined to be the closest user or hero in the vicinity of a location of the individual experiencing the emergency. The HERO application determines that the user having smartphone 1306 does carry or have an identified electronic sleeve associated to an epi pen. The software alerts the user's smartphone with an audible alert or vibration on their smartphone highlighting and pulsing the HERO link. If the individual activates the HERO link the emergency location is identified on the map and the user of smartphone 1306 can get to the user having the emergency and administer the epi pen or give them the epi-pen to inject themselves. In some cases, the user answering the emergency may activate the HERO software to locate and access their local epi-pen via the fob, or the HERO software may be programmed to perform the functions of the fob to find medicines and devices within the short-range wireless network 1301. In most cases of emergency with full use of the present invention, a local medical professional or neighbor having the HERO application can get to and save the life of the user in distress before an ambulance can arrive.

Although users do upload their personal information to server 1305, users may elect to remain anonymous to other users of the HERO application 1309. There are no limits to the number of users, emergency devices, emergency medicines and locations that can be registered and tracked. Heros and medical emergency sufferers may be matched during an emergency in neighborhoods, large stadium venues, sporting events, cruise ships, airports, and inner cities.

Figure 15:
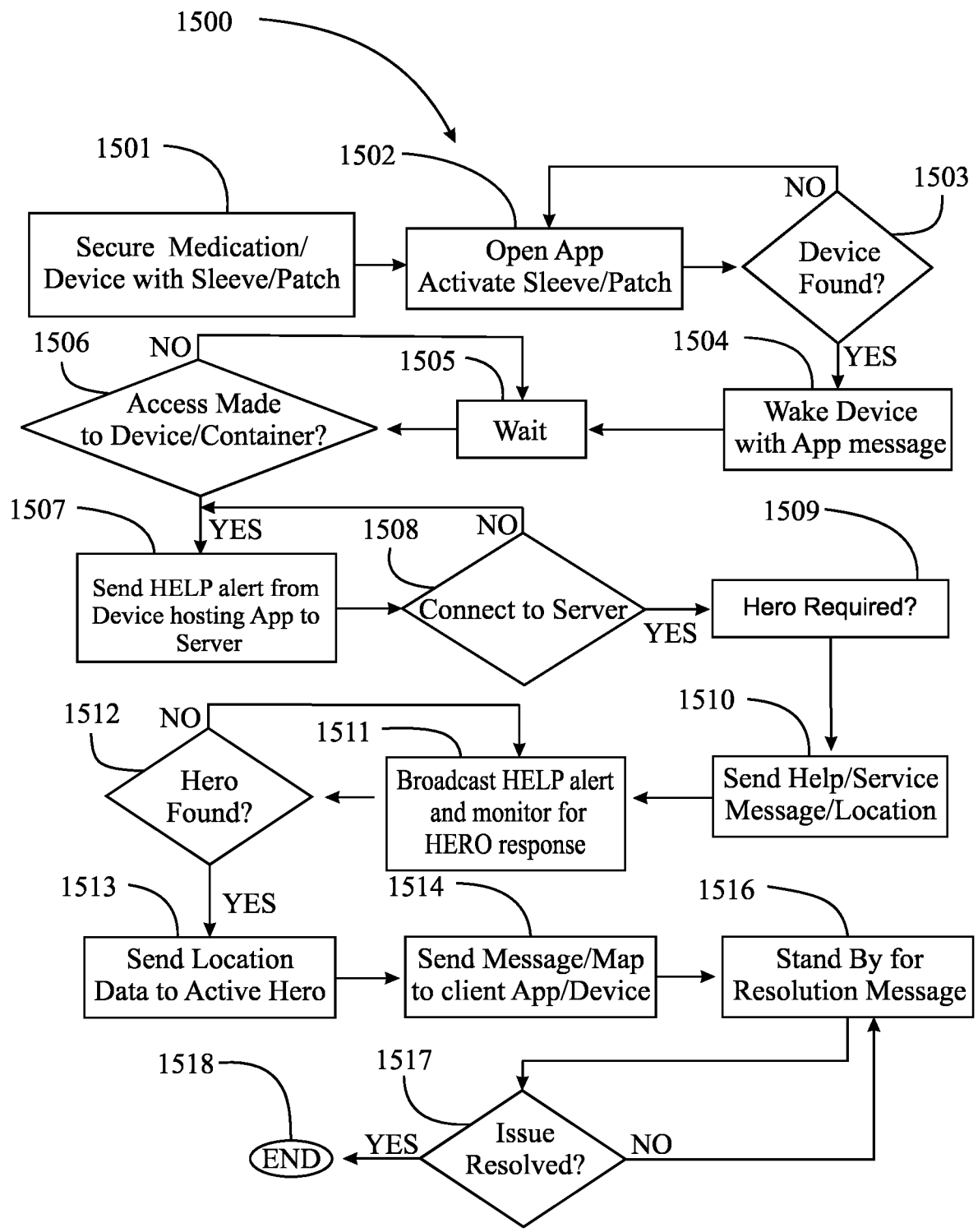
FIG. 15 is an example of software workflow of the application installed on the computerized device.

FIG. 15 is a schematic 1500 of an example workflow and method of operation of the software 1307 and 1309. In step 1501 the emergency medication and/or emergency device is secured with an electronic sleeve or patch. In steps 1502 to 1506 the HERO application is opened, and a connection is established between the application and each electronic sleeve or electronic patch. A registration or serial number is uploaded from the electronic sleeve or patch to the software, or one is assigned. In either case, each electronic sleeve or patch includes a unique identifier in some form, whether it's a serial number, code, etc. which is used to register the sleeve or patch. The patches and sleeves are also associated with the user on the HERO application. In this step we also associate a specific emergency medicine like an EpiPen and inhaler etc. or emergency medical device like a rescue suction device to each electronic patch or sleeve.

At step 1507 a user may activate a HELP alert from the smartphone or computerized device hosting the HERO application and connect to the server at step 1508. The server identifies the user activating the HELP messages and also identifies the medicines and emergency devices that are required in the emergency, based upon stored electronic sleeves and patches and their associated medicines and devices uploaded previously by the users in the registration process. In an event where a user requiring emergency help has more than one emergency medicine registered or more than one emergency device registered, a message is sent through the application to the user requiring help or requiring an emergency to identify which medicine and which device they require.

At step 1509 the server determines that medical assistance or a hero is required. In steps 1510 and 1511 the software continues to broadcast the HELP alert and identify users and their locations with the HERO application. The broadcast from the server may only be sent to the applications on smartphones having registered users willing to help and are in a close or having the closest vicinity to the user having the emergency. Once a user activates the HERO link in their application thereby accepting the role of providing assistance at step 1512, the server sends a message of what medicine medical device is required and the location of the user having the emergency via a map and additional data if required at steps 1513 and 1514. Step by step directions may be audibly provided for the hero user by the application or via text to direct them to the user having the emergency with the quickest route possible. This may be done by association between the hero application and known mapping applications provided by Google, for example.

At step 1516 the server waits for a resolution message response by the hero user or user having the emergency. In a case where there are no users in a close vicinity to provide assistance, the server may contact emergency personnel via 911 or other emergency communication, thereby sending an ambulance or other emergency medical personnel to the location of the user having the emergency. Additionally, if the hero user sent to the location cannot resolve the emergency in a timely manner, the server may also send for an ambulance or other emergency personnel outside of the users subscribed to the HERO application. At step 1517 the server continues to monitor to see if the emergency issue is resolved and ends the process at step 1518 when a resolution message is received, or emergency personnel are dispatched.

It will be apparent to one with skill in the art that the HERO application in communication with smartphones, electronic sleeves and patches of the present invention may be provided using some or all the elements described herein. The arrangement of elements and functionality thereof relative to the software and components of the invention are described in different embodiments, each of which is an implementation of the present invention. While the uses and methods are described in enabling detail herein, it is to be noted that many alterations could be made in the details of the construction and the arrangement of the elements without departing from the spirit and scope of this invention. The present invention is limited only by the breadth of the claims below.

The invention claimed is:

1. A system enabled to assist a user during a medical emergency, comprising:
   a plurality of electronic units each having a unique identifier, adapted to attach, one each, to emergency medication dispensing devices and emergency medical devices including;
      a housing formed by a wall of flexible material having a diameter and a length;
      a microprocessor and associated circuitry encapsulated entirely within a thickness of the wall of the housing, the circuitry including at least a microprocessor, wireless communications capability, a transceiver capable of cellular and satellite communication, and GPS;
      at least one battery encapsulated within the thickness of the wall providing power to the microprocessor and the circuitry;
      alert mechanisms including at least one LED at least partially encapsulated within the wall of the housing and visible from outside of the wall, at least one sound emitter and a vibrating motor;
   an Internet connected server storing and executing software from non-transitory storage medium; and
   a plurality of GPS enabled smartphones storing and executing an instance of the software;
   wherein the instance of the software stored on the smartphones provides a first user and a second user with a user interface enabling the first and second users to subscribe to the software uploading personal identification and location data, enabling the first user to register the unique identifier of one or more first electronic units, of the plurality of electronic units, each first electronic unit associated and adhered to an emergency medication dispenser, identifying the emergency medication being dispensed or an emergency medical device, and enabling the second user to register the unique identifier of one or more second electronic units, of the plurality of electronic units, each second electronic unit associated and adhered to an emergency medication dispenser, identifying the emergency medication being dispensed or an emergency medical device, wherein communication is established between the one or more first and second electronic units, the smartphones and the server and the server is enabled to track location of the first and second electronic units and the smartphones via the GPS.

2. The system of claim 1 wherein the first user requires an emergency medication contained within the emergency medication dispenser or emergency medical device associated with the one or more first electronic units, initiates the alert mechanisms on the first electronic unit via the user interface in order to locate the emergency medication or emergency medical device.

3. The system of claim 2 wherein the first user initiates a medical emergency alert to the server via interaction with an indicia on the user interface based upon an inability to administer the required emergency medication or emergency medical device and the server identifies the emergency medication or emergency medical device registered to the first user and broadcasts an alert to all user interfaces on smartphones associated with second users determined to be within a vicinity of the first user.

4. The system of claim 3, wherein the server identifies and locates the second user within the vicinity having a closest location to the first user, the second user having the registered second electronic unit adhered to an associated second emergency medication dispenser having emergency medication or second emergency medical device matching the emergency medication or emergency medical device required by the first user.

5. The system of claim 4, wherein the second user indicates an ability to assist the first user with the emergency medicine or emergency medical device via interaction with second indicia on the user interface of the second smartphone associated with the second user.

6. The system of claim 5, wherein the indication of ability to assist the first user causes presentation of a map in the user interface of the identified second user directing the identified second user to the location of the first user.

7. The system of claim 4 wherein in an instance where a second user is not within the vicinity, the instance of software on the smartphone alerts emergency medical professionals to the location of the first user.

8. The system of claim 1, wherein the emergency medication dispenser is any dispenser from a list including a cylinder with adjustable regulator, an epi pen, a metered spray bottle, a nasal spray bottle, an oral inhaling device, a syringe and a medication dispenser having an inner volume and a removable cap, the medication dispenser integrated with an electronic unit of the electronic unit.

9. The system of claim 8, wherein the emergency medications are any medication from a list including oxygen, epinephrine, nitroglycerine, diphenhydramine, albuterol/salbutamol, aspirin, glucose, atropine, hydrocortisone, morphine or nitrous oxide, naloxone, lorazepam or midazolam and flumazenil.

10. The system of claim 1, wherein the emergency medical devices are any devices from a list including an automated external defibrillator (AED), a rescue suction device, an oxygen mask, electrosurgical units and a portable ventilator.

11. The system of claim 1, wherein the electronic unit is in a form of a tubular sleeve.

12. The system of claim 1, wherein the electronic unit is in a form of a planar patch enabled to adhere to a surface.

* * * * *